US009782411B2

(12) United States Patent
Briand et al.

(10) Patent No.: US 9,782,411 B2
(45) Date of Patent: Oct. 10, 2017

(54) {4-[5-(3-CHLORO-PHENOXY)-OXAZOLO[5,4-D]PYRIMIDIN-2-YL]-2,6-DIMETHYL-PHENOXY}-ACETIC ACID FOR USE IN THE PREVENTION OR TREATMENT OF ACUTE KIDNEY INJURY

(71) Applicant: Sanofi, Paris (FR)

(72) Inventors: Véronique Briand, Paris (FR); Sabine Gratzer, Paris (FR); Thomas Huebschle, Frankfurt am Main (DE); Philip Janiak, Paris (FR); Dieter Kadereit, Frankfurt am Main (DE); Ashfaq Parkar, Bridgewater, NJ (US); Bruno Poirier, Paris (FR); Matthias Schaefer, Frankfurt am Main (DE); Paulus Wohlfart, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/027,964

(22) PCT Filed: Oct. 15, 2014

(86) PCT No.: PCT/EP2014/072078
§ 371 (c)(1),
(2) Date: Apr. 7, 2016

(87) PCT Pub. No.: WO2015/055694
PCT Pub. Date: Apr. 23, 2015

(65) Prior Publication Data
US 2016/0235756 A1 Aug. 18, 2016

(30) Foreign Application Priority Data

Oct. 15, 2013 (EP) .................................... 13306417

(51) Int. Cl.
*A61K 31/519* (2006.01)
(52) U.S. Cl.
CPC ........... *A61K 31/519* (2013.01); *Y02P 20/582* (2015.11)
(58) Field of Classification Search
CPC .............................. A61K 31/519; C07D 498/04
See application file for complete search history.

(56) References Cited

U.S. PATENT DOCUMENTS

2013/0079358 A1* 3/2013 Kadereit .............. C07D 498/04
514/260.1

FOREIGN PATENT DOCUMENTS

| WO | WO-02/04665 A2 | 1/2002 |
| WO | WO-2004/103306 A2 | 12/2004 |
| WO | WO-2005/054215 A1 | 6/2005 |
| WO | WO-2011/086079 | 7/2011 |

OTHER PUBLICATIONS

Hla et al, Seminars in Cell & Developmental Biology, 2004, 15, 513-520.*
Argraves, K.M. et al. (Sep. 5, 2008, e-published on Jul. 7, 2008). "High Density Lipoprotein-associated Sphingosine 1-Phosphate Promotes Endothelial Barrier Function," *The Journal of Biological Chemistry* 283(36):25074-25081.
Awad, A.S. et al. (2006, e-published on Jan. 10, 2006). "Selective Sphingosine 1-phosphate 1 receptor Activation Reduces Ischemia-reperfusion Injury in Mouse Kidney," *Am. J. Physiol. Renal. Physiol.* 290:F1516-F1524.
Bajwa, A. et al. (2010). "Activation of Sphingosine-1-Phosphate 1 Receptor in the Proximal Tubule Protects Against Ischemia-Reperfusion Injury," *J. Am. Soc. Nephrol.* 21:955-965.
Belvitch, P. et al. (2012, e-published on Sep. 5, 2011). "Role of FAK in S1P-regulated Endothelial Permeability," *Microvascular Research* 83:22-30.
Bonventre, J.V. et al. (2003). "Recent Advances in the Pathophysiology of Ischemic Acute Renal Failure," *J. Am. Soc. Nephrol.* 14:2199-2210.
Brinkman, V. (2007). "Sphingosine 1-phosphate Receptors in Health and Disease: Mechanistic Insights from Gene Deletion Studies and Reverse Pharmacology," *Pharmacology & Therapeutics* 115:84-105.
Burne, M.J. et al. (Nov. 2001). "Identification of the CD4+T Cell as a Major Pathogenic Factor in Ischemic Acute Renal Failure," *The Journal of Clinical Investigation* 108(9):1283-1290.
Camerer, E. et al. (Jul. 2009). "Sphingosine-1-phosphate in the Plasma Compartment Regulates Basal and Inflammation-induced Vascular Leak in Mice," *The Journal of Clinical Investigation* 119(7):1871-1879.
Cao, C. et al. (2010, e-published Aug. 11, 2010). "Intrinsic Nitric Oxide and Superoxide Production Regulates Descending Vasa Recta Contraction," *Am. J. Physiol. Renal. Physiol.* 299:F1056-F1064.
Castelli, W.P. et al. (Nov. 28, 1986). "Incidence of Coronary Heart Disease and Lipoprotein Cholesterol Levels," *The Journal of American Medical Association* 256(20):2835-2838.
Christoffersen, C. et al. (Jun. 7, 2011). "Endothelium-protective Sphingosine-1-phosphate Provided by HDL-associated Apolipoprotein M," *PNAS* 108(23):9613- 9618.
Coca, S.G. et al. (Jun. 2009). "Long-Term Risk of Mortality and Other Adverse Outcomes After Acute Kidney Injury: A Systematic Review and Meta-Analysis," *American Journal of Kidney Disease* 53(6):961-973.
Fliser, D. et al. (2012, e-published Oct. 8, 2012). "A European Renal Best Practice ERBP (European Renal Best Practice) Position Statement on the Kidney Disease Improving Global Outcomes (KDIGO) Clinical Practice Guidelines on Acute Kidney Injury: Part 1: definitions, conservative management and contrast-induced nephropathy," *Nephrol Dial Transplant* 27:4263-4272.
Garcia-Criado, F.J. et al. (Oct. 27, 1998). "Protective Effect of Exogenous Nitric Oxide on the Renal Function and Inflammatory Response in a Model of lschemia-Reperfusion," *Transplantation* 66(8):982-990.

(Continued)

*Primary Examiner* — Sudhakar Katakam
(74) *Attorney, Agent, or Firm* — Morrison & Foerster LLP

(57) ABSTRACT

{4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI (acute kidney injury). Medicament and pharmaceutical composition thereof.

3 Claims, 13 Drawing Sheets

(56) References Cited

OTHER PUBLICATIONS

Figure 2:
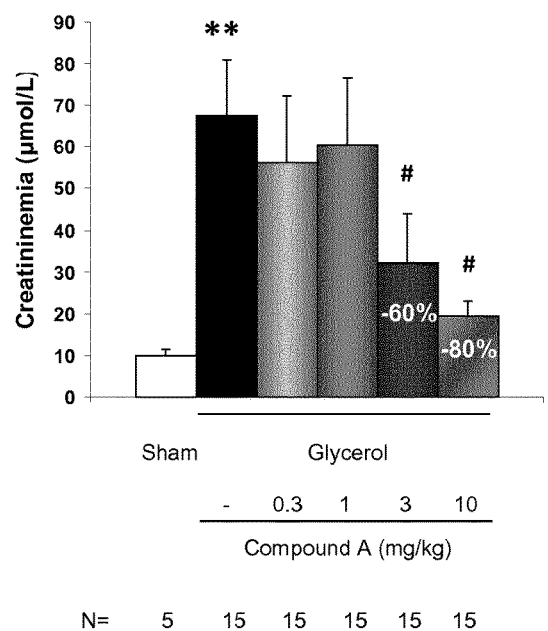

Gonzalez-Cabrera, P.J. et al. (2012). "S1P$_1$ Receptor Modulation with Cyclical Recovery from Lymphopenia Ameliorates Mouse Model of Multiple Sclerosis," *Molecular Pharmacology* 81(2):166-174.

Gergely, P. et al. (2012). "The Selective Sphingosine 1-phosphate Receptor Modulator BAF312 Redirects Lymphocyte Distribution and Has Species-Specific Effects on Heart Rate," *British Journal of Pharmacology* 167(5):1035-1047.

Ham, A. et al. (2014, e-published Sep. 11, 2013). "Selective Deletion of the Endothelial Sphingosine-1-phosphate 1 receptor Exacerbates Kidney Ischemia-reperfusion Injury," *Kidney International* 85:807-823.

Hammad, S.M. et al. (2012). "Sphingosine 1-Phosphate Distribution in Human Plasma: Associations with Lipid Profiles," *Journal of Lipids* 2012:1-8, (eight pages).

Hoste, E. AJ. et al. (2006). "RIFLE Criteria for Acute Kidney Injury are Associated with Hospital Mortality in Critically Ill Patients: a cohort analysis," *Critical Care* 10:R73, ten pages.

Hsu, C.Y. et al. (May 2009, e-published Apr. 30, 2009). "Nonrecovery of Kidney Function and Death after Acute on Chronic Renal Failure," *Clinical Journal of the American Society of Nephrology* 4(5):891-898.

Igarashi, J. et al. (Oct. 13, 2000, e-published on Jul. 31, 2000). "Agonist-modulated Targeting of the EDG-1 Receptor to Plasmalemmal Caveolae," *The Journal of Biological Chemistry* 275(41):32363-32370.

Igarashi, J. et al. (2008, e-published on Jul. 27, 2008). "S1P and eNOS Regulation," *Biochimica et Biophysica Acta* 1781:489-495.

Ishani, A. et al. (2009). "Acute Kidney Injury Increases Risk of ESRD among Elderly," *J. Am. Soc. Nephrol.* 20:223-228.

International Search Report and Written Opinion mailed Dec. 19, 2014, issued in PCT Application No. PCT/EP2014/072078; 12 pages.

Jain, N. et al. (Feb. 28, 2012). "Fingolimod-associated Macular Edema," *Neurology* 78:672-680.

Karuna, R. et al. (2011, e-published on Sep. 6, 2011). "Plasma Levels of Sphingosine-1-phosphate and Apolipoprotein M in Patients with Monogenic Disorders of HDL Metabolism," *Atherosclerosis* 219:855-863.

Kono, M. et al. (Jul. 9, 2004, e-published on May 11, 2004). "The Sphingosine-1-phosphate Receptors S1P$_1$, SiP$_2$, and S1P$_3$ Function Coordinately during Embryonic Angiogenesis," *The Journal of Biological Chemistry* 279(28):29367-29373.

Lai, L.W. et al. (2007, e-published on Mar. 21, 2007) "A Sphingosine-1-phosphate Type 1 Receptor Agonist Inhibits the Early T-cell Transient Following Renal Ischemia-reperfusion Injury," *Kidney International* 71:1223-1231.

Lema, G. et al. (Apr. 2009) "Decreased Nitric Oxide Products in the Urine of Patients Undergoing Cardiac Surgery," *Journal of Cardiothoracic and Vascular Anesthesia* 23(2):188-194.

Lien, Y.HH. et al. (2006, e-published on Mar. 29, 2006) "S1P$_1$-selective Agonist, SEW2871, Ameliorates Ischemic Acute Renal Failure," *Kidney International* 69(9):1601-1608.

Lucke, S. et al. (2010). "Endothelial Functions of Sphingosine-1-phosphate," *Cellular Physiology and Biochemistry* 26:87-96.

Lutz, J. et al. (2008, e-published on Sep. 24, 2008). "The A20 Gene Protects Kidneys from Ischaemia/reperfusion Injury by Suppressing Pro-inflammatory Activation," *J. Mol. Med.* 86:1329-1339.

Mandala, S. et al. (Apr. 12, 2002) "Alteration of Lymphocyte Trafficking by Sphingosine-1-Phosphate Receptor Agonists," *Science* 296:346-349.

McVerry, B.J. et al. (2005, e-published on Sep. 27, 2004). "In Vitro and in Vivo Modulation of Vascular Barrier Integrity by Sphingosine 1-phosphate: Mechanistic Insights," *Cellular Signalling* 17:131-139.

Mehta, R.L. et al. (2004) "Spectrum of Acute Renal Failure in the Intensive Care Unit: The PICARD experience," *Kidney International* 66:1613-1621.

Miller, G.J. et al. (Jan. 4, 1975) "Plasma-High-Density-Lipoprotein Concentration and Development of Ischaemic Heart-Disease," *The Lancet* 1(7897):16-19.

Mizugishi, K. et al. (Dec. 2005) "Essential Role for Sphingosine Kinases in Neural and Vascular Development," *Molecular and Cellular Biology* 25(24):11113-11121.

Morales-Ruiz, M. et al. (Jun. 1, 2001). "Sphinogosine 1-Phosphate Activates Akt, Nitric Oxide Production, and Chemotaxis through a G$_i$ Protein/Phosphoinositide 3-Kinase Pathway in Endothelial Cells," *The Journal of Biological Chemistry* 276(22):19672-19677.

Nakayama, M. et al. (Jun. 8, 1999) "T$^{786}$→C Mutation in the 5'-Flanking Region of the Endothelial Nitric Oxide Synthase Gene is Associated with Coronary Spasm," *Circulation* 99(22):2864-2870.

Nash, K. et al. (May 2002). "Hospital-Acquired Renal Insufficiency," *American Journal of Kidney Diseases* 39(5):930-936.

Okusa, M.D. et al. (2007). "Targeting Sphingosine 1 Phosphate Receptor Type 1 Receptors in Acute Kidney Injury," *Drug Discovery Today: Disease Mechanisms* 4(1):55-59.

Ostermann, M. et al. (2007) "Acute Kidney Injury in the Intensive Care Unit According to RIFLE," *Crit. Care Med.* 35(8):1837-1843.

Popov, A.F. et al. (2009, e-published on Jun. 11, 2009) "The eNOS 786C/T Polymorphism in Cardiac Surgical Patients with Cardiopulmonary Bypass is associated with Renal Dysfunction," *European Journal of Cardio-thoracic Surgery* 36:651-656.

Roviezzo, F. et al. (Feb. 2006, e-published on Dec. 1, 2005) "Essential Requirement for Sphingosine Kinase Activity in eNOS-dependent NO Release and Vasorelaxation," *The FASEB Journal* 20(2):340-342, seventeen pages.

Sadik, N.A.H. et al. (2012, e-published on Aug. 31, 2011). "The Association of Receptor of Advanced Glycated End Products and Inflammatory Mediators Contributes to Endothelial Dysfunction in a Prospective Study of Acute Kidney Injury Patients with Sepsis," *Molecular and Cellular Biochemistry* 359:73-81.

Sanna, M.G. et al. (Apr. 2, 2004, e-published Jan. 19, 2004). "Sphingosine 1-Phosphate (S1P) Receptor Subtypes S1P1 and SIP3, Respectively, Regulate Lymphocyte Recirculation and Heart Rate," *Journal Biological Chemistry* 279(14):13839-13848.

Schmouder, R. et al. (2006) "FTY720: Placebo-Controlled Study of the Effect on Cardiac Rate and Rhythm in Healthy Subjects," *J. Clin. Pharmacol.* 46:895-904.

Shea, B.S. et al. (2010) "Prolonged Exposure to Sphingosine 1-Phosphate Receptor-1 Agonists Exacerbates Vascular Leak, Fibrosis, and Mortality after Lung Injury," *American Journal of Respiratory Cell and Molecular Biology* 43:662-673.

Singbartl, K. et al. (2000) "Protection from Ischemia-reperfusion Induced Severe Acute Renal Failure by Blocking E-selectin," *Crit. Care Med* 28(7):2507-2514.

Uchino, S. et al. (Aug. 17, 2005). "Acute Renal Failure in Critically Ill Patients," *The Journal of American Medical Association* 294(7):813-818.

Uchino, S. et al. (2006). "An Assessment of the RIFLE Criteria for Acute Renal Failure in Hospitalized Patients," *Crit. Care Med.* 34(7):1913-1917.

Wang, L. et al. (2009, e-published on Sep. 30, 2008). "Regulation of Vascular Permeability by Sphingosine 1-Phosphate," *Microvascular Research* 77:39-45.

Wilkerson, B.A. et al. (Dec. 28, 2012, e-published on Nov. 7, 2012). "Sphingosine 1-Phospate (S1P) Carrier-dependent Regulation of Endothelial Barrier," *The Journal of Biological Chemistry* 287(53):44645-44653.

Ysebaert, D.K. et al. (Aug. 2004). "T Cells as Mediators in Renal Ischemia/Reperfusion Injury," *Kidney International* 66(2):491-496.

Zhu, Q. et al. (Jul. 2011, e-published on Apr. 6, 2011) "A Novel Lipid Natriuretic Factor in the Renal Medulla: Sphingosine-1-Phosphate," *Am. J. Physiol. Renal Physiol.* 301(1):F35-F41.

* cited by examiner

FIG 1-A
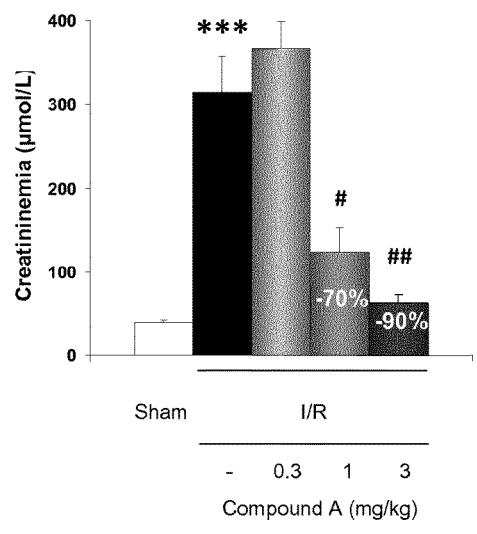
FIG 1-B
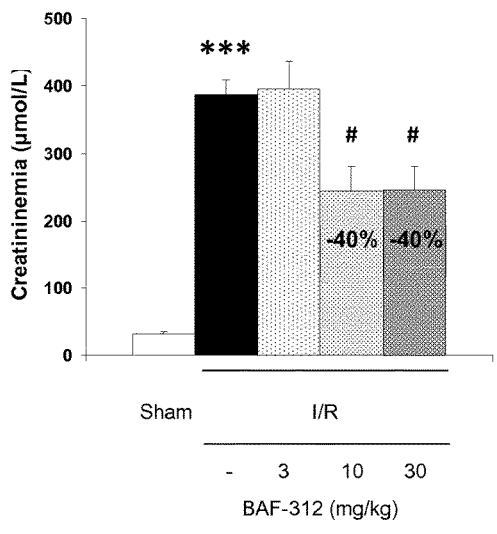
FIG 1-C
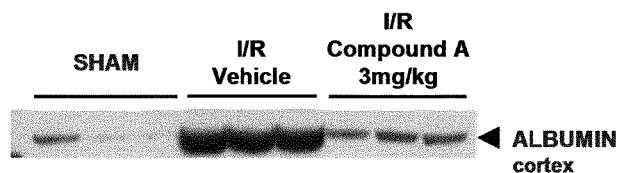

FIG 1-D
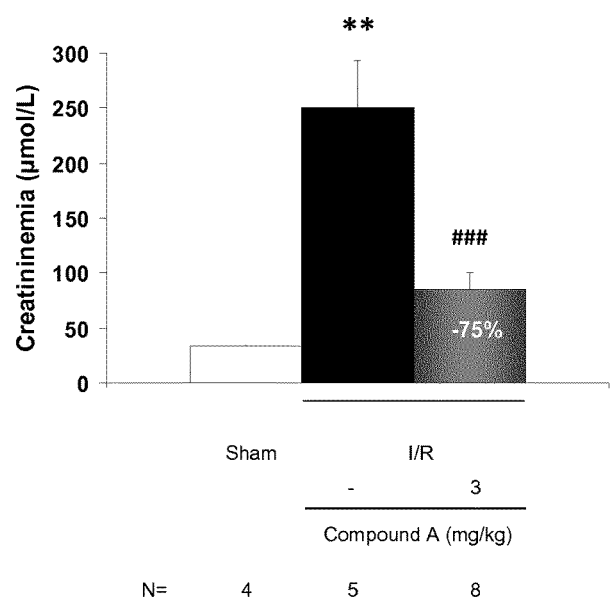

FIG 3-A
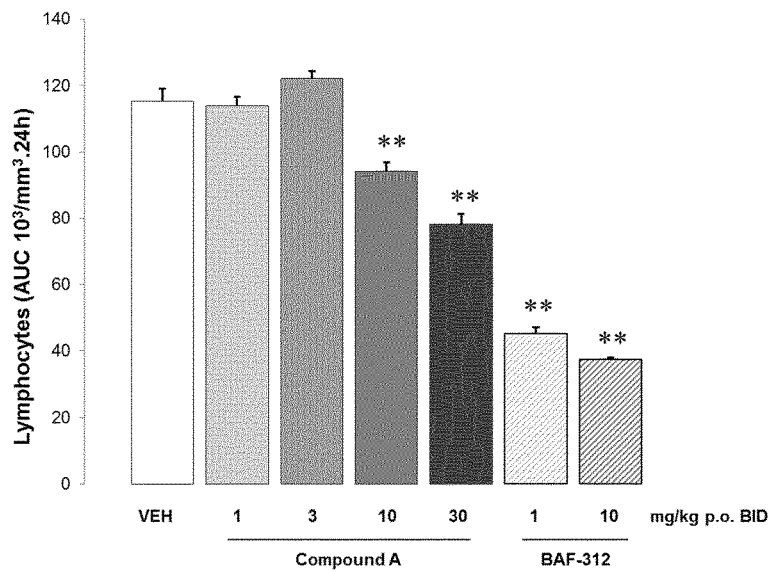
FIG 3-B- Single oral administration
FIG 3-C- Repeated oral administration
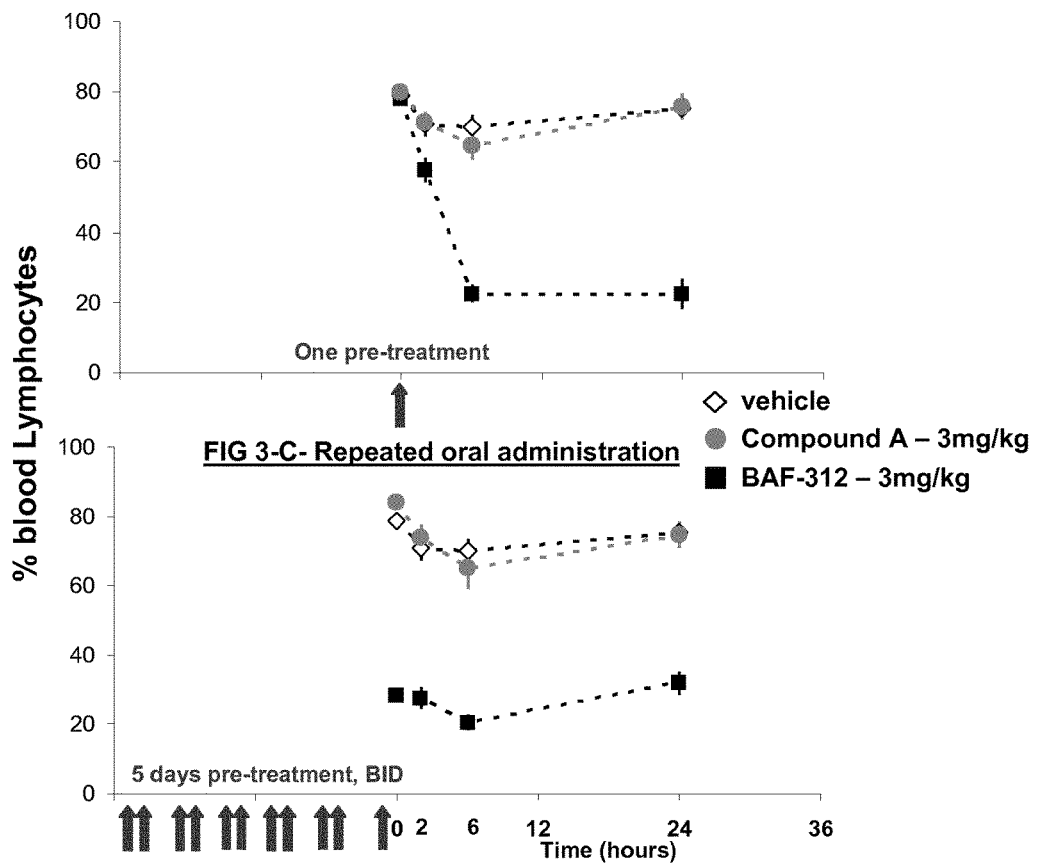

FIG 3-D
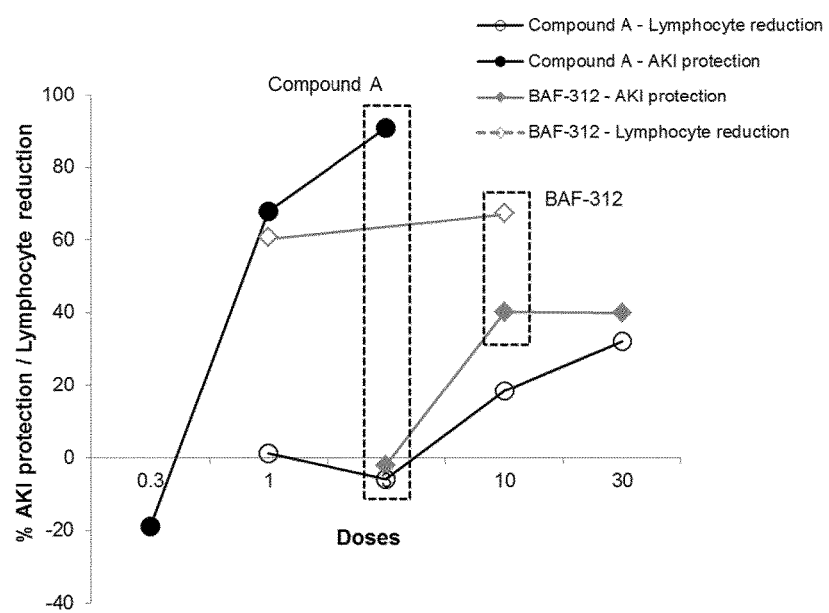

FIG 5-A
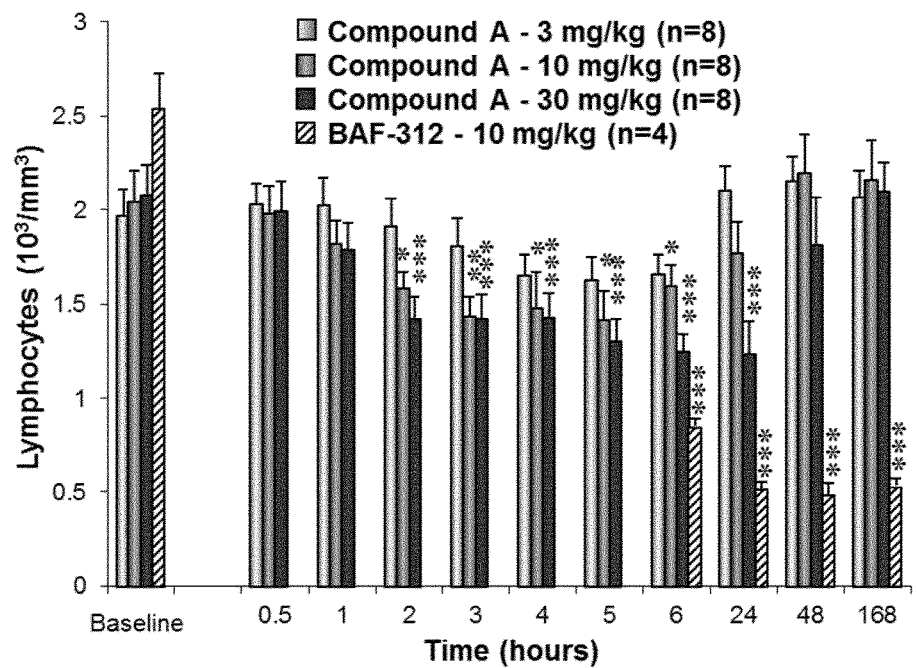
FIG 5-B
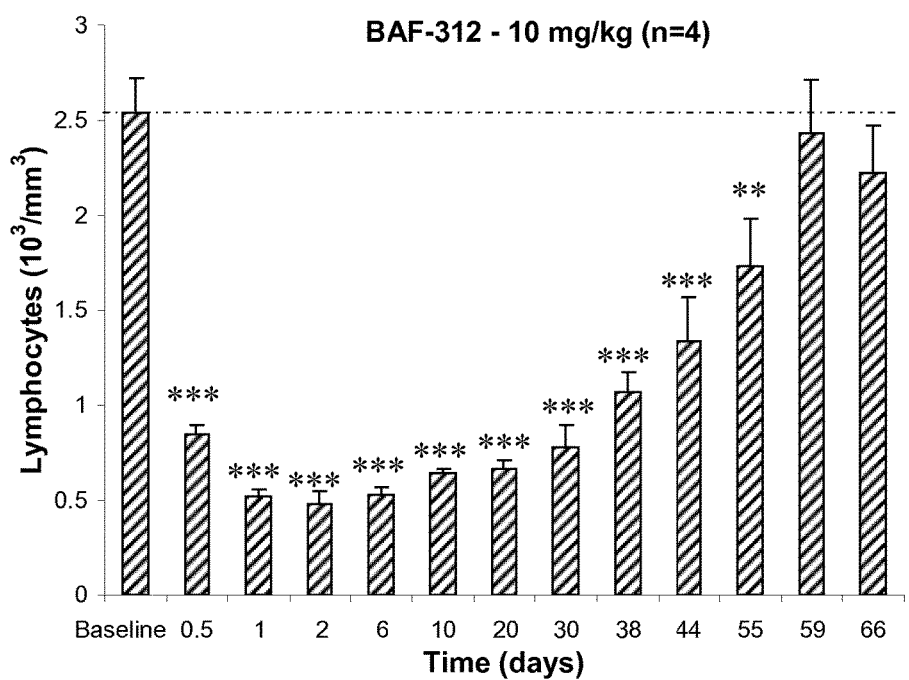

FIG 6-A
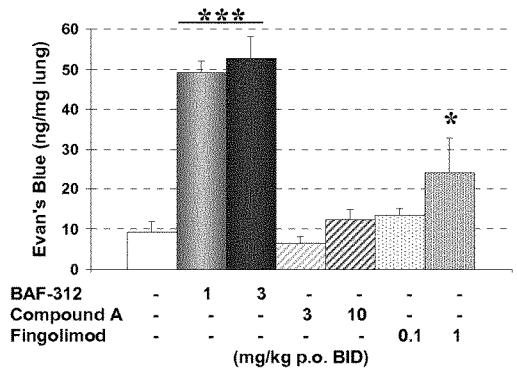
FIG 6-B
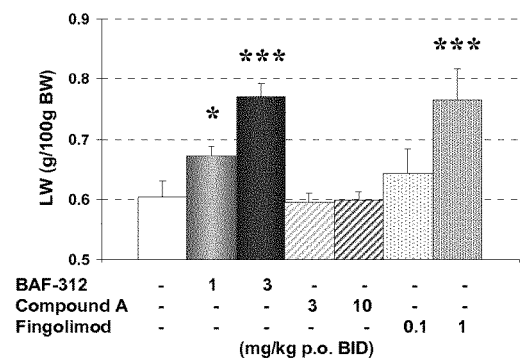
FIG 6-C
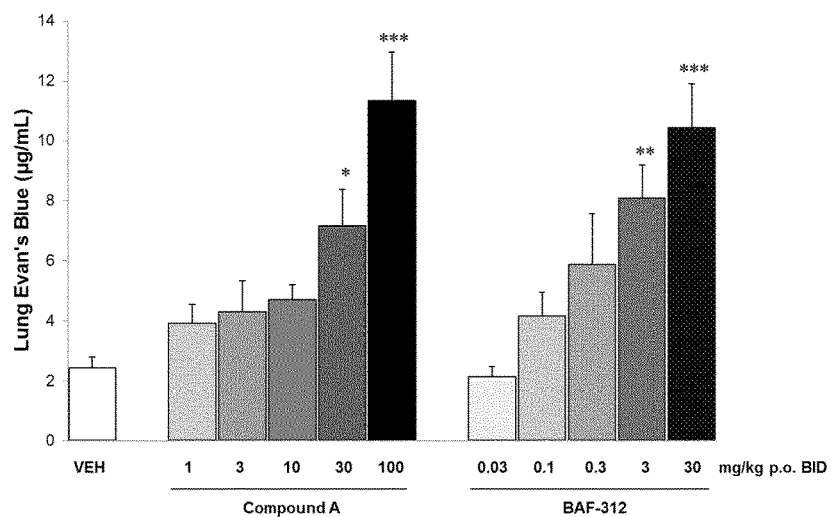

FIG 8-A
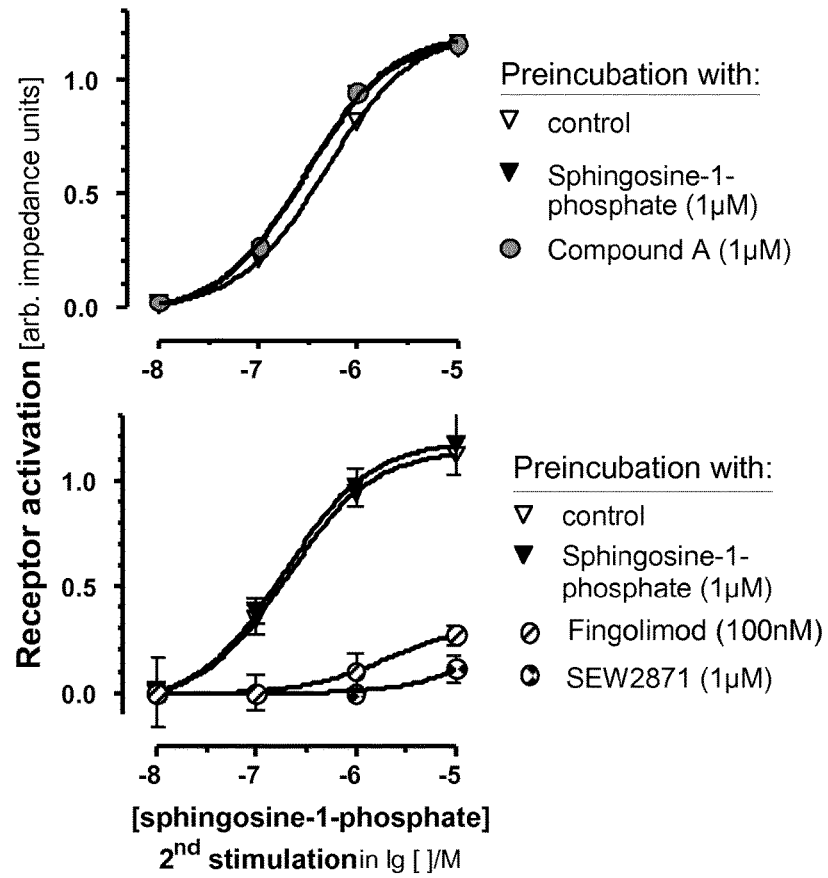
FIG 8-B
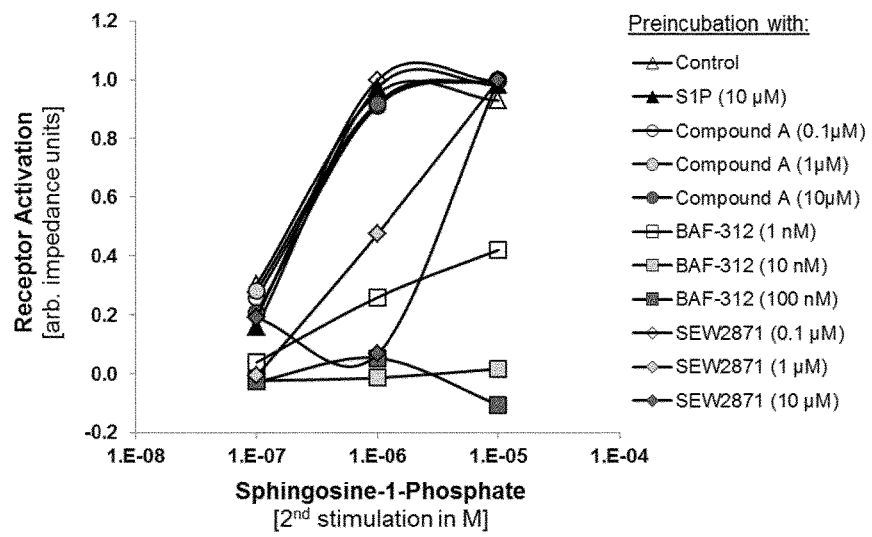

FIG 9-A
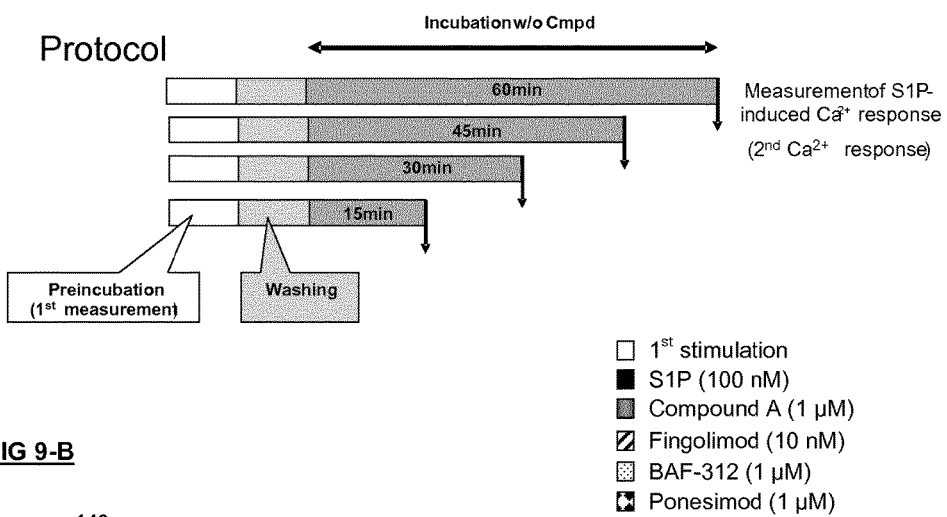
FIG 9-B
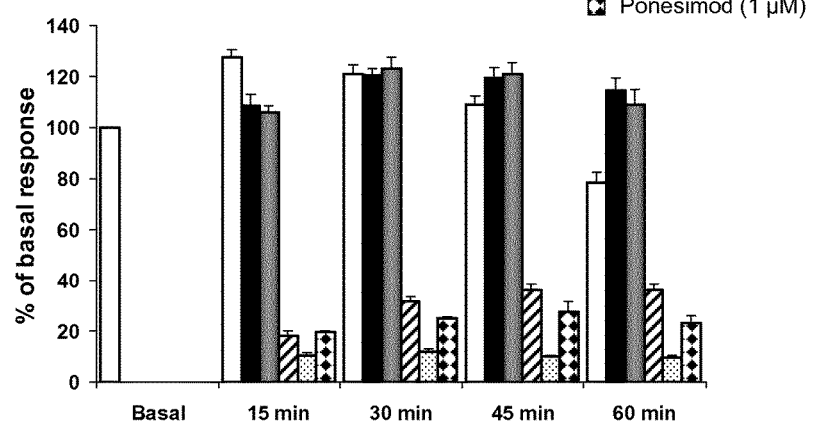

FIG 10-A
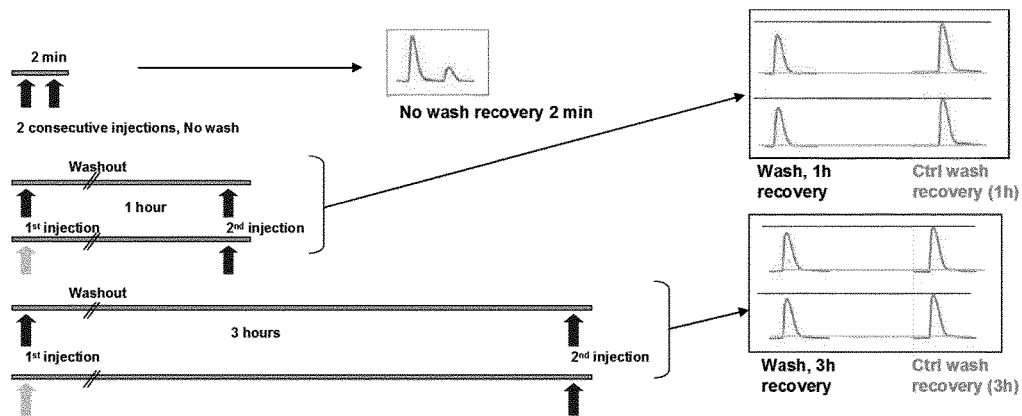
FIG 10-B
1 hour washout
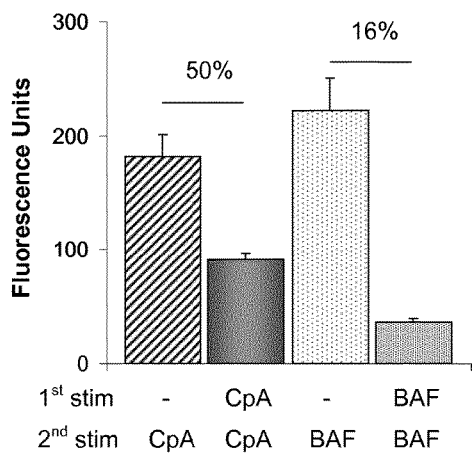
3 hours washout
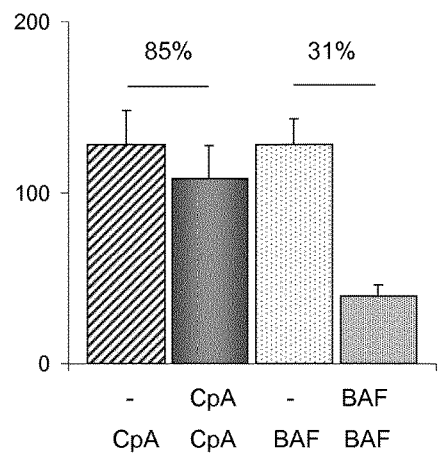

{4-[5-(3-CHLORO-PHENOXY)-OXAZOLO[5,4-D]PYRIMIDIN-2-YL]-2,6-DIMETHYL-PHENOXY}-ACETIC ACID FOR USE IN THE PREVENTION OR TREATMENT OF ACUTE KIDNEY INJURY

CROSS REFERENCE TO RELATED APPLICATIONS

This application is a National Phase application under 35 U.S.C. §371 of International Application No. PCT/EP2014/072078 filed Oct. 15, 2014, which claims priority benefit to EP Application No. 13306417.0 filed Oct. 15, 2013, the disclosures of each of which are herein incorporated by reference in their entirety.

The present invention relates to {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of acute kidney injury (AKI), and a pharmaceutical composition thereof. The compound {4-[5-(3-chloro-phenoxy)-oxazolo[5,4-d]pyrimidin-2-yl]-2,6-dimethyl-phenoxy}-acetic acid or a pharmaceutically acceptable salt thereof and a preparative method thereof are described in the patent application WO2011/086079. This compound has affinity for S1P1/EDG1 receptors.

Acute kidney injury (AKI), formerly known as "acute renal failure" is a frequent and potentially severe disorder that occurs in a variety of settings with clinical manifestations ranging from transient elevation in serum creatinine (SCr) to anuric definitive renal failure. AKI has been traditionally described as an abrupt (within 48 hours) decrease in kidney function as measured by increases in serum creatinine. The recent KDIGO (Kidney Disease Improving Global Outcomes) guidelines established consensus around the diagnostic criteria based on laboratory and clinical values listed below (Working group of ERBP (European Renal Best Practice), 2012, NDT 27: 4263-4272). AKI is defined and staged as any of the following:

Increase in SCr by ≥0.3 mg/dL (26.5 μmol/L) within 48 hours; or

Increase in SCr to 1.5 times baseline, which is known or presumed to have occurred within the prior 7 days; or Urine volume <0.5 mL/kg/h for 6 hours.

AKI occurs in approximately 7% of all hospitalized patients (Nash et al., 2002, Am J Kidney Dis 39: 930-936) and up to 36-67% of critically ill patients, depending on the definition used. Severe AKI occurs in 4-25% of all Intensive Care Unit (ICU) admissions and about 5% of ICU patients with AKI require renal replacement therapy (Hoste et al. 2006, Crit Care 10: R73, Mehta et al., 2004, Kidney Int 66: 1613-1621; Uchino et al., 2005, Jama 294: 813-818; Uchino et al., 2006, Crit Care Med 34: 1913-1917; Ostermann et al., 2007, Crit Care Med 35: 1837-1843). The most common causes of AKI are sepsis, major surgery, hypovolemia and medications. Risk factors for development of AKI include old age (>75 yrs), chronic kidney disease (CKD, eGFR (estimated Glomerular Filtration Rate) <60 mL/min/1.73 $m^2$), atherosclerotic peripheral vascular disease, cardiac failure, liver disease, diabetes mellitus and nephrotoxic medications.

Despite advances in preventive strategies and support measures, AKI continues to be associated with high morbidity and mortality, particularly in those admitted to the ICU, where in-hospital mortality rates may exceed 50%. In addition to mortality rates, there are chronic consequences which include a high risk of developing chronic kidney disease (CKD) and hastened development of end-stage renal disease (ESRD) (Hsu et al., 2009, Clin J Am Soc Nephrol 4: 891-898; Ishani et al., 2009, JASN 20: 223-228; Coca et al., 2009, Am J Kidney Dis 53: 961-973). Morbidity is also associated with increased costs and increased length of hospital stay.

There is a clear unmet medical need since there is no approved therapy for the prevention or for the treatment of AKI whatever the aetiology. Management of the condition is primarily supportive, with Renal Replacement Therapy (RRT) as the central component of care for patients with severe AKI. Hydration remains the most appropriate preventative measure for contrast induced nephropathy (CIN).

Sphingosine-1-phosphate (S1P) is a lipid mediator that binds to five GPCRs (G Protein-Coupled Receptors) termed $S1P_{1-5}$ (Brinkman et al., 2007, Pharmacol Ther 115: 84-105). Circulating S1P originates mainly from endothelial cells, platelets and erythrocytes and is found highly bound to plasma proteins including ApoM (Apolipoprotein M) in HDL (High Density Lipoproteins) (Hammad et al., 2012, J Lipids; Karuna et al., 2011, Atherosclerosis 219: 855-863) and albumin. $S1P_1$ is widely expressed, including in endothelial, immune, and renal epithelial cells. $S1P_1$ regulates many physiological functions including maintenance of endothelial barrier integrity (cytoskeleton rearrangements), cell growth, survival, differentiation, angiogenesis and immune cell trafficking. $S1P_1$ is highly expressed in the renal medulla (Zhu et al., 2011, Am J Physiol Renal Physiol 301: F35-F41), a region of the kidney where blood flow and oxygen supply are restricted by the tubulo-vascular anatomy specifically designed for urinary concentration. Since cells in this region have high oxygen consumption, the medulla is particularly vulnerable to hypoxic damage. Cortical tubular damage is a consequence of both medulla injury and direct insults on proximal tubular cells. $S1P_1$ is up-regulated following renal ischemia reperfusion injury (Awad et al., 2006, Am J Physiol Renal Physiol 290: F1516-F1524) and its activation is expected to preserve renal function by three main mechanisms:

Maintenance of endothelial barrier function. This barrier is damaged in AKI leading to impaired vascular permeability and adhesion properties, Limitation of apoptosis of proximal tubular epithelial cells, Reduction of inflammatory cell infiltration. Inflammation in AKI is often a consequence of the combined injury to tubular epithelial cells and the endothelial barrier.

The role of the S1P-$S1P_1$ pathway in regulating endothelial barrier integrity has been extensively documented (Wang and Dudek, 2009, Microvasc Res 77: 39-45; Mc Verry and Garcia, 2005, Cell signalling 17: 131-139; Lucke and Levkau, 2010, Cell Phys Biochem 26: 87-96). Activation of $S1P_1$ improves endothelial barrier function through PLC/$Ca^{2+}$/FAK/pRac pathway activation (Belvitch and Dudek, 2012, Microvasc Res 83: 22-30). HDL-ApoM associated S1P was shown to prolong endothelial barrier function through eNOS activation (Wilkerson et al., 2012, JBC 287: 44645-44653; Christoffersen et al., 2011, PNAS 108: 9613-9618; Argraves et al., 2008, JBC 283: 25074-25081). In this regard, low plasma HDL levels have been associated with a risk of developing AKI in patients undergoing vascular surgery (Miller G J and Miller N E., 1975, Lancet 1:16-19; Castelli W P, Garrison R J, Wilson P W, et al., 1986, JAMA; 256:2835-2838)

Global or endothelial-specific deletion of $S1P_1$ induces embryo-lethality due to a massive haemorrhage affecting multiple organs (Kono et al., 2004, JBC 279: 29367-29373). Identical defects are seen in knockout mice with deletion of the enzymes responsible for S1P biosynthesis (sphingosine kinases 1 and 2) (Mizugishi et al., 2005, Mol Cell Biol 25: 11113-11121). Similarly, $S1P_1$ antagonists also increase vascular permeability. Despite acute protective effects of $S1P_1$ functional antagonists in AKI models (Bajwa et al., 2010, JASN 21: 955-965; Awad et al., 2006, Am J Physiol Renal Physiol 290: F1516-F1524), chronic treatment with these $S1P_1$ functional antagonists dramatically worsens vascular leak in lung injury models and disrupts endothelial barrier integrity in vitro (Shea et al., 2010, Am J Respir Cell Mol Biol 43: 662-673). Similar endothelial defects are also mimicked in S1P less mice (Camerer et al., 2009, JCI 119: 1871-1879).

In patients and AKI models, cytokines like TNF-α are released from endothelial cells and up-regulate adhesion molecules such as ICAM-1, VCAM-1 and P/E-selectins which contribute to inflammatory cell infiltration into the tubulo-interstitial parenchyma (Bonventre et al., 2003, JASN 14: 2199-2210; Singbartl et al., 2000, Crit Care Med 28: 2507-2514; Sadik et al, 2012, Mol Cell Biochem 359: 73-81). Moreover, in cultured human endothelial cells, several of these endothelial adhesion molecules are up-regulated after hypoxia/re-oxygenation (Lutz et al., 2008, J Mol Med 86: 1329-1339). $S1P_1$ activation down-regulates these adhesion molecules and therefore reduces inflammatory cells infiltration (Lien et al., 2006, Kidney Int 69: 1601-1608). An essential role for S1P in preserving endothelial function in acute kidney injury has been demonstrated using a conditional deletion of the endothelial $S1P_1$ receptor in mice (Ham A., 2013, Kidney Int, Sept).

Stimulation of $S1P_1$ activates endothelial nitric oxide synthase (eNOS) through Akt phosphorylation, which is a key enzyme regulating local vasorelaxation via the production of NO (Morales-Ruiz et al., 2001, JBC 276: 19672-19677; Igarashi et al, 2000, JBC 275: 32363-32370; Igarashi et al, 2008, BBA 1781: 489-495). Therefore, $S1P_1$ induces vasorelaxation in an endothelium and NO-dependent manner (Roviezzo et al., 2006, FASEB J 20: 340). NO has a protective effect on renal function in animal models of I/R-induced AKI (Garcia-Criado et al, 1998, Transplantation 66: 982-990). In rats, eNOS inhibition reduces renal blood flow by 35%, with coupled decreases in GFR and increased renal vascular resistance (Cao et al, 2010, Am J Physiol Renal Physiol 299: F1056-F1064). S1P is regarded as one of the most effective activators of endothelial nitric oxide, which is known to improve local blood flow, but also to limit platelet activation and vascular congestion, particularly in the vulnerable cortico-medullary region. This mechanism could be of importance to preserve renal function during AKI. Importantly, reduced nitric oxide bioavailability is associated with AKI in cardio-pulmonary by-pass (CPB) and sepsis patients (Lema et al., 2009, J Cardio Thorac Vasc Anesth 23:188-194; Sadik et al., 2012, Mol Cell Biochem 359: 73-81). Interestingly, a 786C polymorphism in the human eNOS promoter exhibits reduced transcriptional activity and is associated with renal dysfunction in cardiac surgery patients with cardio-pulmonary bypass (Popov et al., 2009, Eur J Cardio-Thorac Surgery 36: 651-656; Nakayama et al., 1999, Circulation 99: 2864-2870). The polymorphism frequency is around 50% and might represent a significant sub-population that is not only more at risk of developing AKI but also more responsive to a treatment that restores local NO levels, such as through activation of $S1P_1$.

Moreover, activation of $S1P_1$ limits directly apoptosis of proximal tubular epithelial cells by activating pERK and pAkt survival pathways. Specific deletion of $S1P_1$ in proximal tubular epithelial cells worsens renal dysfunction following ischemia-reperfusion injury (Bajwa et al., 2010, JASN 21: 955-965), as well as tubular necrosis, which underline an endogenous S1P tone buffering the severity of reperfusion injury. These data underscore the importance of a protective role for the $S1P-S1P_1$ system in AKI, both on endothelial and epithelial axes.

S1P is responsible for the egress of lymphocytes from the lymph node to the blood through $S1P_1$ activation. This $S1P_1$ activation causes receptor internalization followed by recycling of the receptor back to the cell surface, allowing re-activation. However, $S1P_1$ functional antagonists or antagonists are believed to cause lymphopenia by either inhibiting the recycling of internalised $S1P_1$ receptors back to the cell surface or blocking $S1P_1$ activation, and hence cause dramatic and sustained reductions in cell surface $S1P_1$. Consequently, the latter agents show a large and sustained drop in blood lymphocytes as observed preclinically and clinically.

Several reports show that T lymphocytes contribute to acute kidney injury. The observation that injury is ameliorated by depletion of T cells and reconstituted with adoptive transfer of CD4+ T cells is evidence that it is dependent on CD4+ T cells (Burne et al., 2001, J. Clin Invest 108: 1283-1290; Ysebaert et al., 2004, Kidney Int 66: 491-496). It is therefore not surprising that $S1P_1$ functional antagonists, including fingolimod and SEW2871, are protective in acute kidney injury models at lymphopenic doses (Lien et al., 2006, Kidney Int 69: 1601-1608).

However, lymphopenia is a predisposing factor for opportunistic infections, particularly in very sensitive, debilitated patients such as patients at high risk of AKI (old age, cardiac diseases, diabetes and chronic kidney disease). There is consequently a need for a selective $S1P_1$ agonist which induces limited lymphopenia, or in the best case, no lymphopenia, and has therapeutic utility in the treatment of AKI. Surprisingly, the compound {4-[5-(3-chloro-phenoxy)-oxazolo[5,4-d]pyrimidin-2-yl]-2,6-dimethyl-phenoxy}-acetic acid differs from other $S1P_1$ modulators, by the fact that it causes AKI protection in mammals at doses that are non-lymphopenic. It is believed that this property of {4-[5-(3-chloro-phenoxy)-oxazolo[5,4-d]pyrimidin-2-yl]-2,6-dimethyl-phenoxy}-acetic acid might be related to its biased agonism at the $S1P_1$ receptor, with minimal functional antagonism or desensitization effects. This would represent a significant clinical safety advantage for the use of {4-[5-(3-chloro-phenoxy)-oxazolo[5,4-d]pyrimidin-2-yl]-2,6-dimethyl-phenoxy}-acetic acid in the treatment of AKI.

SUMMARY OF INVENTION

The present invention concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI (acute kidney injury).

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use wherein {4-[5-(3-chloro-phenoxy)-oxazolo[5,4-d]pyrimidin-2-yl]-2,6-dimethyl-phenoxy}-acetic acid does not induce lymphopenia when an AKI protective dose is administered and induces limited lymphopenia when a higher dose is administered.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use as a non lymphopenic agent in the prevention or treatment of AKI.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI with no lymphopenic effect when an AKI protective dose is administered.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use as above-described wherein {4-[5-(3-chloro-phenoxy)-oxazolo[5,4-d]pyrimidin-2-yl]-2,6-dimethyl-phenoxy}-acetic acid is AKI protective when a non lymphopenic dose is administered.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI (acute kidney injury), wherein {4-[5-(3-chloro-phenoxy)-oxazolo[5,4-d]pyrimidin-2-yl]-2,6-dimethyl-phenoxy}-acetic acid is a selective $S1P_1$ agonist which does not induce receptor desensitization.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI (acute kidney injury), wherein {4-[5-(3-chloro-phenoxy)-oxazolo[5,4-d]pyrimidin-2-yl]-2,6-dimethyl-phenoxy}-acetic acid is a selective $S1P_1$ agonist which is non-lymphopenic at AKI protective doses.

The present invention also concerns {4-[5-(3-chloro-phenoxy)-oxazolo[5,4-d]pyrimidin-2-yl]-2,6-dimethyl-phenoxy}-acetic acid or a pharmaceutically acceptable salt thereof for use without lymphopenic effect in the prevention or treatment of AKI.

The present invention also relates to a medicament comprising as an active ingredient {4-[5-(3-chloro-phenoxy)-oxazolo[5,4-d]pyrimidin-2-yl]-2,6-dimethyl-phenoxy}-acetic acid or a pharmaceutically acceptable salt thereof.

The present invention also relates to a pharmaceutical composition comprising as an active ingredient {4-[5-(3-chloro-phenoxy)-oxazolo[5,4-d]pyrimidin-2-yl]-2,6-dimethyl-phenoxy}-acetic acid or a pharmaceutically acceptable salt thereof and a pharmaceutically acceptable excipient for use in the prevention or treatment of AKI.

The present invention also relates to an article of manufacture comprising:
  a packaging material;
  a pharmaceutical composition comprising {4-[5-(3-chloro-phenoxy)-oxazolo[5,4-d]pyrimidin-2-yl]-2,6-dimethyl-phenoxy}-acetic acid or a pharmaceutically acceptable salt thereof as an active ingredient and a pharmaceutically acceptable excipient; and
  a label or package insert contained within the packaging material indicating that a patient can be treated for AKI with the pharmaceutical composition.

The invention also concerns a method of treating AKI in a patient in need thereof comprising administering to said patient a therapeutically effective amount of {4-[5-(3-chloro-phenoxy)-oxazolo[5,4-d]pyrimidin-2-yl]-2,6-dimethyl-phenoxy}-acetic acid or a pharmaceutically acceptable salt thereof.

The invention also concerns a method of treating AKI in a patient in need thereof comprising administering to said patient a therapeutically effective amount of {4-[5-(3-chloro-phenoxy)-oxazolo[5,4-d]pyrimidin-2-yl]-2,6-dimethyl-phenoxy}-acetic acid or a pharmaceutically acceptable salt thereof, wherein {4-[5-(3-chloro-phenoxy)-oxazolo[5,4-d]pyrimidin-2-yl]-2,6-dimethyl-phenoxy}-acetic acid has no lymphopenic effect.

The invention also concerns a method of treating AKI in a patient in need thereof comprising administering to said patient a therapeutically effective amount of {4-[5-(3-chloro-phenoxy)-oxazolo[5,4-d]pyrimidin-2-yl]-2,6-dimethyl-phenoxy}-acetic acid or a pharmaceutically acceptable salt thereof, wherein {4-[5-(3-chloro-phenoxy)-oxazolo[5,4-d]pyrimidin-2-yl]-2,6-dimethyl-phenoxy}-acetic acid has no lymphopenic effect when an AKI protective dose is administered.

The invention also concerns a method of treating AKI in a patient in need thereof comprising administering to said patient a therapeutically effective amount of {4-[5-(3-chloro-phenoxy)-oxazolo[5,4-d]pyrimidin-2-yl]-2,6-dimethyl-phenoxy}-acetic acid or a pharmaceutically acceptable salt thereof wherein the treatment is prophylactic.

The present invention also relates to an article of manufacture wherein the label or package insert contained within the packaging material indicating that a patient can be treated for AKI with the above mentioned pharmaceutical composition without lymphopenic effect.

The present invention relates to an article of manufacture wherein the label or package insert contained within the packaging material indicating that a patient can be treated for AKI with the above mentioned pharmaceutical composition without lymphopenic effect wherein the treatment is prophylactic.

Definitions

For convenience reasons and to facilitate reading, the compound {4-[5-(3-chloro-phenoxy)-oxazolo[5,4-d]pyrimidin-2-yl]-2,6-dimethyl-phenoxy}-acetic acid has been renamed as "compound A" in the chapters of the current application and in the figures.

For the present invention the following words are to be understood accordingly:
  Selective $S1P_1$ agonist is a compound that is more potent on $S1P_1$ compared to the other 4 S1P receptors, $S1P_{2-5}$. In addition the compound should have minimal or no activity in a broad range of receptor, enzyme and ion channel assays.
  Lymphopenia is the condition of having an abnormal drop of blood lymphocytes, a white blood cell with important functions in the immune system. In adults, a lymphocyte level below 1,500 cells/microliter is diagnostic (proof of the condition), and in children, a lymphocyte level below 3,000 cells/microliter is diagnostic.
  Lymphopenia mediated by $S1P_1$ activation refers to a lymphopenic condition caused by using an $S1P_1$ modulator. Since S1P is responsible for $S1P_1$-mediated egress of lymphocytes from the lymph node to the blood, the latter agents are believed to cause lymphopenia by either inhibiting the recycling of internalised $S1P_1$ receptors back to the cell surface or blocking $S1P_1$ activation.
  Limited lymphopenia is a transient reduction of blood lymphocytes (absolute lymphocyte count falling outside of the normal range before treatment). Transient refers to a temporal change in lymphocytes that returns to the normal range within 24 h or 48 h.
  Non-lymphopenic or no lymphopenia refers to a lack of transient or sustained reduction of blood lymphocytes (absolute lymphocyte count falling outside of the normal range before treatment). Transient refers to a temporal change in lymphocytes that returns to the normal range within 24 h, whereas sustained refers to a reduction that persists beyond 24 h.

AKI protective dose: a dose of {4-[5-(3-chloro-phenoxy)-oxazolo[5,4-d]pyrimidin-2-yl]-2,6-dimethyl-phenoxy}-acetic acid which provides a significant reduction of plasma creatinine of at least 30%.

Therapeutically effective amount, as used herein, means an amount of a pharmaceutical compound, such as {4-[5-(3-chloro-phenoxy)-oxazolo[5,4-d]pyrimidin-2-yl]-2,6-dimethyl-phenoxy}-acetic acid that produces an effect on AKI.

Patient means a human patient.

Prophylactic: which serves to prevent or protect against an undesired effect and is intended to prevent a medical condition from occurring, especially a disease.

A first embodiment is {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI, wherein {4-[5-(3-chloro-phenoxy)-oxazolo[5,4-d]pyrimidin-2-yl]-2,6-dimethyl-phenoxy}-acetic acid is non-lymphopenic at AKI protective doses.

A second embodiment is {4-[5-(3-chloro-phenoxy)-oxazolo[5,4-d]pyrimidin-2-yl]-2,6-dimethyl-phenoxy}-acetic acid or a pharmaceutically acceptable salt thereof for use in the prevention or treatment of AKI, wherein the protective effects are mediated by $S1P_1$ activation without inducing lymphopenia.

Another embodiment is an article of manufacture as described above, wherein the label or package insert contained within the packaging material indicating that patients receiving the treatment with the above mentioned pharmaceutical composition can be treated for AKI without inducing lymphopenia.

ABBREVIATIONS

AKI Acute Kidney Injury
ApoM Apolipoprotein M
CIN Contrast Induced Nephropathy
CKD Chronic Kidney Disease
DMSO Dimethylsulfoxide
ERBP European Renal Best Practice
eGFR estimated Glomerular Filtration Rate
eNOS endothelial Nitric Oxide Synthase
ESRD End-Stage Renal Disease
FlipR Fluorescence Imaging Plate Reader
GPCRs G Protein-Coupled Receptors
HDL High Density Lipoproteins
HDMEC Human Dermal Microvascular Endothelial Cells
HSC Hepatic Stellate Cells
ICU Intensive Care Unit
I/R Ischemia/Reperfusion
KDIGO Kidney Disease Improving Global Outcomes
PBS Phosphate Buffer Saline
RRT Renal Replacement Therapy
S1P Sphingosine-1-Phosphate
$S1P_1$ Sphingosine-1-Phosphate 1
SCr Serum Creatinine
s.e.m standard error of mean

EXAMPLES

The following examples further illustrate the present invention and are not intended to limit the invention. For convenient reasons and to facilitate reading, the compound {4-[5-(3-chloro-phenoxy)-oxazolo[5,4-d]pyrimidin-2-yl]-2,6-dimethyl-phenoxy}-acetic acid has been renamed as "compound A" into the figures and the results.

Statistical analyses and p values calculation have been performed and are symbolized either by "*" or "#" symbols in the figures, depending on the experimental conditions.

FIG. 1: Effect of a single or repeated administration of compound A and/or BAF-312 in rat Ischemia-Reperfusion (I/R) model. Fischer rats were subjected to sham surgery or to 25 min bilateral renal artery occlusion and plasma creatinine measured following 24 h reperfusion. (FIG. 1-A) Compound A was evaluated at 0.3, 1 and 3 mg/kg p.o. given 1 hour before occlusion. (FIG. 1-B) BAF-312 was evaluated at 3, 10 and 30 mg/kg p.o. given 1 hour before occlusion. The no compound control group was given vehicle 1 hour before occlusion. *$p<0.001$ I/R-vehicle vs Sham group. #$p<0.05$; ##$p<0.01$ compound-treated vs vehicle group. Bars are mean+/−s.e.m. (FIG. 1-C) Kidney samples were collected to evaluate the effect of compound A on cortical albumin content following rat I/R injury. Albumin was measured by Western Blot in cortical area of representative kidneys from sham-operated, I/R-vehicle-treated or I/R-compound A (3 mg/kg p.o.)-treated rats. (FIG. 1-D) Compound A (3 mg/kg p.o.) or vehicle were administrated twice a day for 5 days. The last administration was given 1 hour before occlusion. $p<0.01$ I/R-vehicle vs Sham group. ###$p<0.001$ compound A-treated vs vehicle group. Bars are mean+/−s.e.m.

FIG. 2: Effect of compound A on rhabdomyolysis-induced AKI injury in mice. Compound A (0.3, 1, 3 and 10 mg/kg) or vehicle were administered orally 1 hour prior to intramuscular injection (hindlimbs) of glycerol (50% in PBS v/v) at 8 mL/kg in male CD1 mice. The sham group received the corresponding volume of PBS. Plasma creatinine was evaluated 24 h later. **$p<0.01$ glycerol-vehicle vs Sham group. #$p<0.05$ compound A-treated vs vehicle group. Bars are mean+/−s.e.m.

FIG. 3: Peripheral blood lymphocytes in Fischer rats after single administration (FIG. 3-A) or Sprague-Dawley rats after (FIG. 3-B) single administration or (FIG. 3-C) repeated administration. Compound A was administered orally either at 1, 3, 10 and 30 mg/kg in Fischer rats or 3 mg/kg in Sprague-Dawley rats. BAF-312 was given orally either at 1 and 10 mg/kg in Fischer rats or 3 mg/kg in Sprague-Dawley rats (n=8). In the repeated administration protocol, compounds were administered for 5 days b.i.d. Blood lymphocytes are either expressed as area under curve (AUC) (FIG. 3-A) or as a percentage of total white blood cells at each time point (FIG. 3-B/C), and represented as mean+/−s.e.m. **$p<0.01$ vs baseline. (FIG. 3-D) Relationship between AKI protection and lymphopenia in Fischer rats. Note boxes which denote lack of lymphopenia and full AKI protection for compound A at 3 mg/kg, whereas BAF-312 is lymphopenic and shows partial AKI protection.

Figure 4:
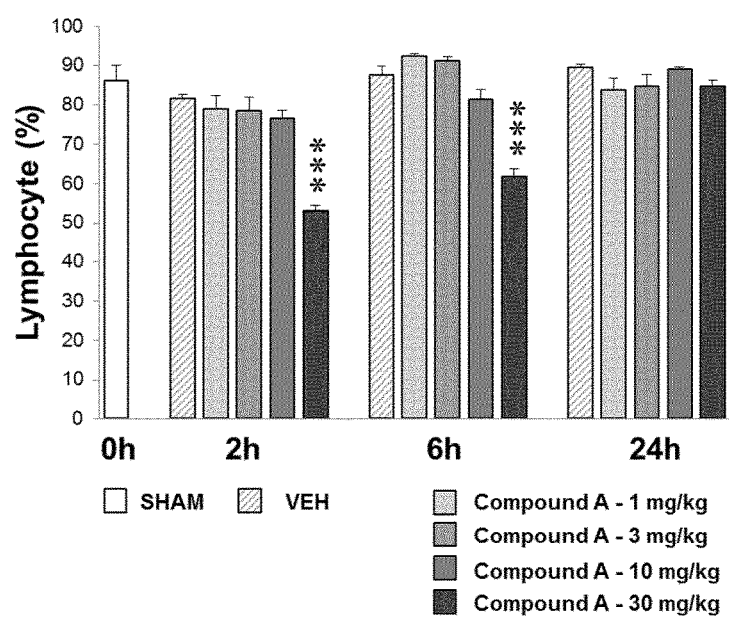

FIG. 4: Peripheral blood lymphocytes in C57Bl6/J mice. Compound A was administered at 1, 3, 10 and 30 mg/kg p.o. (n=8). Blood lymphocytes at each time point are expressed as a percentage of total white blood cells and represented as mean+/−s.e.m. ***$p<0.001$ vs baseline.

FIG. 5: Peripheral blood lymphocytes in beagle dogs. Baseline lymphocyte counts were taken and then dogs were administered a single oral dose of compound A, at 3, 10 and 30 mg/kg (n=8), or BAF-312, at 10 mg/kg (n=4). Animals were monitored for 7 days (FIG. 5-A) and, in the case of BAF-312, for up to 66 days (FIG. 5-B). *$p<0.05$; $p<0.01$; *$p<0.001$ vs baseline. Bars are mean+/−s.e.m. Note compound A did not induce any significant lymphopenia at any of the time points measured for 3 mg/kg dosing.

FIG. 6: Lung vascular leak in healthy C57Bl6/J mice and Fischer rats. Mice were treated for 7 days with compound A (3 and 10 mg/kg p.o. b.i.d.), BAF-312 (1 and 3 mg/kg p.o. b.i.d.) and fingolimod (0.1 and 1 mg/kg p.o. b.i.d.), n=5-8. (FIG. 6-A) Vascular permeability evaluated using Evan's blue extravasation. (FIG. 6-B) Lung weight. Rats were treated for 7 days with compound A (1, 3, 10, 30 and 100 mg/kg p.o. b.i.d.) and BAF-312 (0.03, 0.1, 0.3, 3 and 30 mg/kg p.o. b.i.d.). (FIG. 6-C) Vascular permeability evaluated using Evan's blue extravasation. *p<0.05;  p<0.01; *p<0.001 vs control (no compound) for mice or vehicle (methylcellulose 0.6%—tween 80 0.5% in water) for rats. Bars are mean+/−s.e.m.

Figure 7:
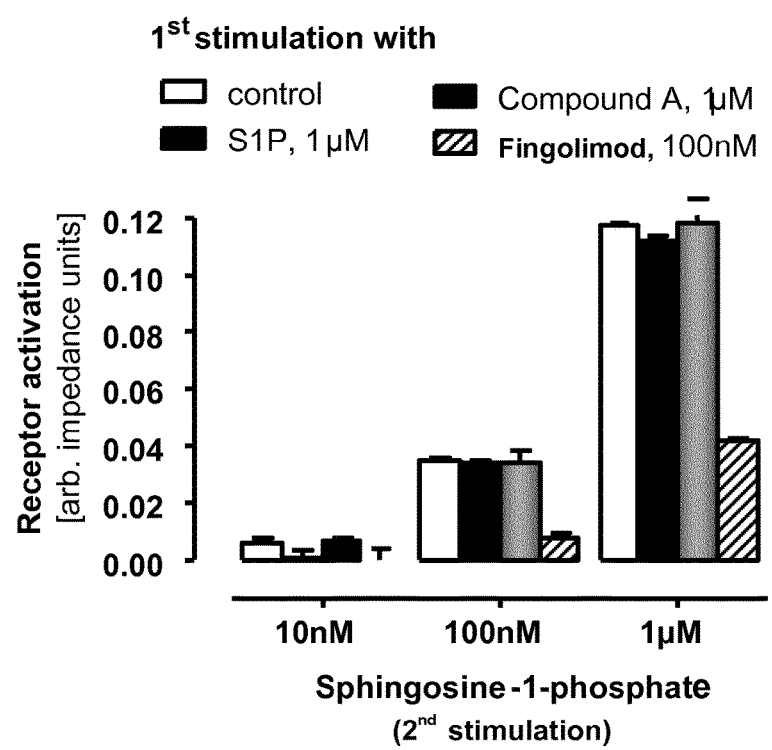

FIG. 7: $S1P_1$ receptor desensitization on human dermal microvascular endothelial cells (HDMEC) using an impedance assay. HDMECs were $1^{st}$ stimulated for 1 h with either S1P (1 µM), fingolimod (100 nM) or compound A (1 µM), followed by a 30 min washout period. The effect of the $1^{st}$ stimulation on receptor desensitization was assessed using a $2^{nd}$ stimulation of S1P (3 concentrations) and measuring the resulting impedance (n=3 experiments). All $1^{st}$ stimulation concentrations were $>EC_{90}$. Bars are mean+/−s.e.m.

FIG. 8: $S1P_1$ receptor desensitization on human umbilical vein endothelial cells (HUVEC) using an impedance assay. HUVECs were $1^{st}$ stimulated for 1 h with either S1P (1 µM), compound A (1 µM), fingolimod (100 nM) or SEW2871 (1 µM), followed by a 30 min washout period. The effect of the $1^{st}$ stimulation on receptor desensitization was assessed using a $2^{nd}$ stimulation of S1P (4 concentrations) and measuring the resulting impedance (n=3 experiments). All $1^{st}$ stimulation concentrations were $>EC_{90}$. Bars are mean+/−s.e.m.

FIG. 9: $S1P_1$ receptor desensitization on CHO cells overexpressing $S1P_1$ (G-fusion) using a FlipR assay. (FIG. 9-A) The protocol involved a 5 minutes $1^{st}$ stimulation with S1P (100 nM), compound A, fingolimod, BAF-312, ponesimod at the indicated concentrations. All $1^{st}$ stimulation concentrations were chosen to be $>EC_{90}$. After varying washout periods, receptor desensitization was assessed using a $2^{nd}$ stimulation with S1P (100 nM). (FIG. 9-B) The S1P-induced FlipR response, expressed as a percentage of the basal response is displayed for each compound with varying wash-out periods (15 to 60 min, n=4 experiments). Bars are mean+/−s.e.m.

FIG. 10: $S1P_1$ receptor desensitization in human hepatic stellate cells (HSC) using a FlipR assay. (FIG. 10-A) The protocol involved a $1^{st}$ stimulation with compound A (10 µM) or BAF-312 (300 nM). All $1^{st}$ stimulation concentrations were chosen to be $>EC_{90}$. After either 1 hour or 3 hours washout periods, receptor desensitization was assessed using a $2^{nd}$ stimulation with the same compound. (FIG. 10-B) The compound A or BAF-312 induced FlipR response, expressed as fluorescent units is displayed for each compound with varying wash-out periods (n=3 experiments). Bars are mean+/−s.e.m.

Figure 11:
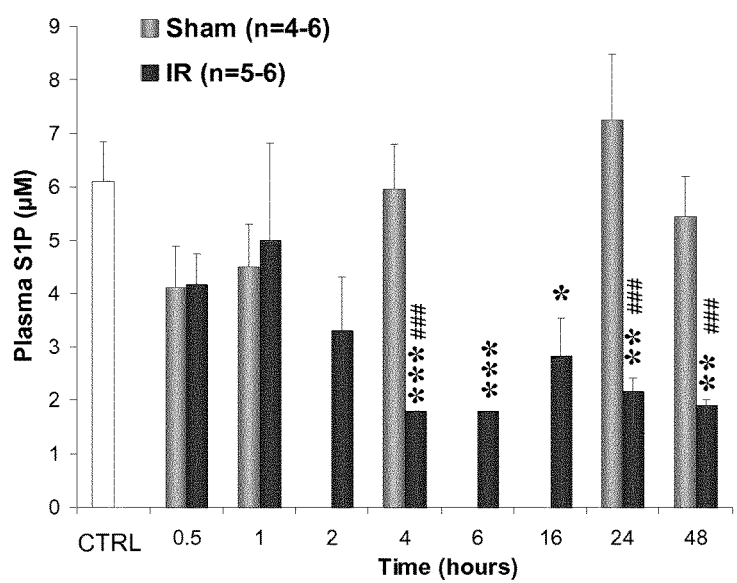

FIG. 11: Time-course of plasma S1P following I/R injury in C57Bl6/J mice. Plasma S1P levels (Elisa kit from Echelon) were evaluated following sham surgery or after 22 min bilateral renal artery occlusion followed by reperfusion. The control group (CTRL) did not undergo surgery. ###p<0.001 vs sham group (time-paired). *p<0.05; p<0.001; *p<0.001 vs control (CTRL). Bars are mean+/−s.e.m.

METHODS

Materials:
Fingolimod and SEW2871 are commercially available. BAF-312 and ponesimod were synthesized according to published methods:
WO04/103306 for BAF-312,
WO05/054215 for ponesimod.
Compound A has been synthesized according to methods described in WO2011/086079 document.
All in vivo studies were performed in accordance with the European Community Standards on the Care and Use of Laboratory Animals and approved by the Animal Care and Use Committee of Sanofi Research & Development.
Statistical Analyses:
On the basis of the normality of the distribution and the homogeneity of variance (Levene test), a Student test or Wilcoxon test was used to compare sham/control group to vehicle-treated group in order to assess differences on the evaluated parameter. Then a one-way analysis of variance (ANOVA) or two-way ANOVA was performed, using Everst@t V6 software, to compare vehicle-treated group to compound-treated group(s). This primary analysis was followed by a Dunnett post hoc test when appropriate. In case of non-homogeneity of variance, a Kruskal-Wallis test was applied. Differences between groups were considered significant if p<0.05.

1. Cardiovascular Function Safety
   a) hERG Assay
   Recombinant CHO (Chinese Hamster Ovary) cell line expressing the human ERG (ether-a-go-go related gene) potassium channel (Cytomyx Catalogue Number: CYL3002) has been cultured according to the following protocol. When necessary a culture has been restarted from frozen aliquots. The aliquots of frozen cells (1 mL) were rapidly warmed to 37° C. and first replated in a 75 cm² flask (Corning). The volume was then adjusted to 10 mL with the α-Minimum Essential Medium (Gibco 32571-028) containing 10% fetal calf serum. The medium has been renewed after 24 h and 1% geneticin (G418, Gibco 10131) has been added to prevent cellular derivation. After two or three days, the cells were sown at $1.5 \times 10^6$ cells by T25 flask. The flasks were placed in 37° C. 5% CO2 incubator during 1 hour; after they have been placed at 28° C. in a 5% $CO_2$ incubator during 2 days. The procedure for cell isolation was carried out after 2 days incubation at 28° C. Cells were harvested with Accumax (Sigma; 1:4) or versene (Gibco) and placed in extracellular medium.
   The cells were superfused with the extracellular solution PATCH (NaCl, 138 mM; KCl, 4 mM; $CaCl_2$, 1.8 mM; $MgCl_2$, 1 mM; glucose, 5.6 mM, HEPES, 10 mM). The pH is adjusted to 7.3 with NaOH. The osmolarity is adjusted to 285 mOsm. The internal solution was prepared as following: KCl, 60 mM; KF, 70 mM; NaCl, 15 mM; HEPES, 5 mM; EGTA(K), 5 mM; pH was adjusted to 7.25 with KOH. The osmolarity is adjusted to 290 mOsm.
   The hERG current was activated in response to voltage steps (2 s) from a holding potential of −80 mV to a test potential of +20 mV followed by a repolarization to −100 mV. Voltage steps were applied at 20 s intervals. hERG current was measured as the tail deactivating current at −100 mV. After a 3 minutes period for baseline measurements, compound A effects were measured 4-6 minutes after the change of solution. At the end of each experiment, the superfusion of a specific hERG-blocker, i.e. Risperidone (which exhibits an $IC_{50}$ around 0.7 µM), at a 10 µM concentration allowed to measure a 100% inhibition of hERG.

The currents were analyzed using a database and analysis software DataXpress 1.0 (Axon Instruments/Molecular Devices). The linear rundown of currents was extrapolated from baseline measurement period and the percentage of hERG current inhibition after drug effect has been calculated as follows:

Percentage of hERG current inhibition (%)=100−
[((I−Irisperidone)/((baseline−(risperidone))×
100].

Where "I" was the current measured after drug effect, "Irisperidone" was the current measured after the effect of the specific hERG-blocker and "Ibaseline" was the current measured before the superfusion of drug.

b) Rabbit Purkinje Fibers Assay

The effects of compound A on resting membrane potential and action potential parameters recorded from isolated rabbit Purkinje fibers (male, New Zealand rabbits; 1.3 to 1.5 kg; 9-12 weeks of age) were evaluated through a microelectrode technique. The following parameters were measured: resting potential (RP in mV), action potential amplitude (APA in mV), maximal rate of rise of action potential ($V_{max}$ in V/s), action potential duration at 50 and 90% of repolarization ($APD_{50}$ and $APD_{90}$ in ms). The fibers were superfused with an oxygenated physiological solution containing (in mmol/L): NaCl, 120; KCl, 4; $MgCl_2$, 1; $NaH_2PO_4$, 1.8; $NaHCO_3$, 25; glucose, 11; $CaCl_2$, 1.8; pH=7.4, at 36±1° C. Compound A was first dissolved into DMSO to obtain a 12 mmol/L stock solution. This solution was further diluted into DMSO and then added into the physiological solution to obtain the appropriate nominal concentrations of 0.3, 1, 3, 10 and 30 µmol/L (i.e., 0.1, 0.5, 1.4, 4.5 and 13.6 µg/mL of active ingredient, respectively). The final concentration of DMSO in the test formulation was kept constant at 0.25% (v/v) in the physiological solution. Purkinje fibers (n=4) were first superfused by the physiological solution. After a 30-minute control period, test compound was evaluated at increasing concentrations sequentially applied, every 30 minutes. For each tested concentration, the fibers were stimulated at the basal rate of 1 pulse per second (1 Hz). In addition, stimulation rate was decreased from 1 pulse per second (1 Hz) to 1 pulse every 4 seconds (0.25 Hz) for 3 minutes, increased again to 1 pulse per second for 1 minute and finally increased to 3 pulses per second (3 Hz) for 2 additional minutes (between the $19^{th}$ and the $25^{th}$ minute), as described below:

c) Dog Telemetry Studies

The purpose of this study was to assess the potential effect of compound A on the cardiovascular function (blood pressure, heart rate and ECG) in conscious telemetered dogs over a 24-hour period post dosing.

Conscious freely moving dogs (Marshall Farms, n=4, 2 males and 2 females, 6.9 to 10.8 kg body weight and 44 to 64-months) received an oral or intravenous dose of the negative control article (i.e., aqueous solution of 0.5% (w/w) hydroxyethylcellulose/0.6% (w/w) polysorbate 80 for oral route, or aqueous solution of 20% Captisol, pH 7.5 to 8) followed by compound A at 30 and 100 mg/kg for oral route as suspensions in negative control article, or 10 and 30 mg/kg for i.v. route as solution in negative control article, according to a rising dose study design with at least a 4-day washout period between each administration (5 mL/kg for oral route or for 30-min infusion into the jugular vein). Arterial blood pressure and lead II ECG signals (Transmitters from Data Science, USA) were continuously recorded on each treatment day from approximately 2 hours before dosing up to 24 hours after dosing. The following parameters were analyzed at several time points: arterial blood pressure (systolic, diastolic and mean), heart rate, electrocardiographic parameters of RR, PQ (=PR), QT interval durations and QRS complex duration as well as body temperature. QT interval was corrected for heart rate variations according to both Fridericia's and van de Water's formulae. The whole ECG signal was examined beat to beat for any rhythm disturbances and waveform morphology from 30 min to 6 h post dosing. On each treatment day, clinical observations were conducted. A video recording was reviewed to identify potential gross behavioural changes and potential interference with cardiovascular parameters. After dosing, the time-points for analysis were as follows: 0.5, 1, 2, 3, 4, 6, 8, 12, 16 and 24 hours.

2. Differentiation on Endothelial Barrier Integrity a) Lung Vascular Leak Study in Mouse Male C57Bl6/J mice (n=5-8, 25-30 g) (Charles River Laboratory, France) were treated, orally and twice a day, for 7 days with compound A at 3 and 10 mg/kg, BAF-312 at 1 and 3 mg/kg, fingolimod at 0.1 and 1 mg/kg or vehicle article (methylcellulose 0.6%—tween 80 0.5% in water) within a volume of administration of 10 mL/kg. The number of mice included in each group was between 5 and 8. After 7 days, mice were anesthetized using an i.p. injection of ketamine (100 mg/kg) and xylasine (10 mg/kg) mixture. Evans blue was injected i.v. in the jugular vein at 15 mg/kg in 1 mL/kg. Ten minutes later, physiological serum was

| TIME (min) | 19 | 3 | 1 | 2 | 5 | 19 | 3 | 1 | 2 | 5 | 19 |
|---|---|---|---|---|---|---|---|---|---|---|---|
| measurement period | | * | * | * | | | * | * | * | | |
| stimulation rate (Hz) | 1 | | 1 | 3 | 1 | 1 | 1 | | 1 | 3 | 1 | 1 |
| | | 0.25 | | | | | 0.25 | | | | |
| | Control Period (30 min) | | | | | Compound 1st concentration (30 min) | | | | | 2nd C (30 min) |

The low stimulation rate was used to favour the occurrence of abnormal electrical events during the repolarization phase of the action potential and to facilitate the development of Early After Depolarization's (EADs). The high stimulation rate was used to evaluate the use-dependent sodium channel blockade. After the highest concentration, the physiological solution was superfused again to evaluate the reversibility of the drug effect (washout).

injected by the left ventricle to rinse the body from residual intravascular Evans blue. Lung tissue was collected and weighted and then immersed in a pure formamide solution during 24 h to extract tissue Evans blue and therefore evaluate vascular permeability. Evans blue concentration was evaluated at 630 nM using a standard curve and normalized with lung weight. Results are expressed as means+/−s.e.m.

b) Lung Vascular Leak Study in Rat

Male Fischer rats (n=4-8, 280-350 g) (Charles River Laboratory, France) were treated, orally and twice a day, for 7 days with compound A (1, 3, 10, 30 and 100 mg/kg), BAF-312 (0.03, 0.1, 0.3, 3 and 30 mg/kg) or vehicle article (methylcellulose 0.6%—tween 80 0.5% in water) within a volume of administration of 2 mL/kg. After 7 days, rats were anesthetized using an i.p. injection of pentobarbital (50 mg/kg). Evans blue was injected i.v. in the retro-orbital sinus at 30 mg/kg in 1 mL/kg. Fifteen minutes later, physiological serum was injected by the left ventricle to rinse the body from residual intravascular Evans blue. Lung tissue was collected and weighted and then immersed in a pure formamide solution (4 mL/g tissue weight) during 24 h to extract tissue Evans blue and therefore evaluate vascular permeability. Evans blue concentration was evaluated at 630 nM using a standard curve. Results are expressed as means+/−s.e.m.

3. Differentiation on Lymphopenic Activity a) Rat Lymphopenia Studies

Male Sprague-Dawley rats (n=8, 250 to 350 g) (Charles River Laboratory, France) received oral administration of compound A, BAF-312 at 3 mg/kg or vehicle article (methylcellulose 0.6%—tween 80 0.5% in water) within a volume of administration of 2 mL/kg. Two protocols were used: single administration or repeated b.i.d. administration during 5 consecutive days. Blood was collected at 2, 6 and 24 h following compound administration (last administration for the repeated protocol) for haematology analysis to determine whole blood lymphocyte count. Results are expressed as mean+/−s.e.m.

Male Fischer rats (n=8, 250 to 350 g) (Charles River Laboratory, France) received a single oral administration of compound A (1, 3, 10 and 30 mg/kg), BAF-312 (1 and 10 mg/kg) or vehicle article (methylcellulose 0.6%—tween 80 0.5% in water) within a volume of administration of 2 mL/kg. Blood was collected at 2, 6 and 24 h following compound administration for haematology analysis to determine whole blood lymphocyte count. Results are expressed as mean+/−s.e.m.

b) Mouse Lymphopenia Studies

Male C57Bl6/J mice (n=8, 25-30 g) (Charles River Laboratory, France) received a single oral administration of compound A at 1, 3, 10 and 30 mg/kg or vehicle article (methylcellulose 0.6%—tween 80 0.5% in water) within a volume of administration of 10 mL/kg. Blood was collected at 2, 6 and 24 h following compound administration for haematology analysis to determine whole blood lymphocyte count. Results are expressed as mean+/−s.e.m.

c) Dog Lymphopenia Studies

Conscious freely moving male dogs (Marshall Farms, n=8, 10.5 to 14.3 kg body weight) received an oral dose of the negative control article (i.e., aqueous solution of 0.5% (w/w) hydroxyethylcellulose/0.6% (w/w) polysorbate 80) or compound A at 3, 10 and 30 mg/kg or BAF-312 at 10 mg/kg, as suspensions in negative control article, according to a rising dose study design with at least a 7-day washout period between each administration (5 mL/kg). Blood was collected at 0.5, 1, 2, 3, 4, 5, 6, 24, 48 and 168 h for both compounds (and up to 66 days for BAF-312) for haematology analysis to determine whole blood lymphocytes count. Results are expressed as mean+/−s.e.m.

4. In Vitro Pharmacology a) Calcium Mobilization (FlipR) Assay in Chinese Hamster Ovarian (CHO) Cells, Chem Cells and HSC 1. CHO Cells Activities of Compound A, BAF-312 and fingolimod were tested on Flp-In stable transfection with $hS1P_1$-G-fusion construction in CHO cells (proprietary), and selectivity tested over $hS1P_2$- and $hS1P_3$-G-fusion constructions (proprietary). Cell line generation is described in WO2011/086079.

The activation of the $S1P_1$ receptor by the compounds was quantified by their effect on $S1P_1$ receptor-related calcium liberation in a cell-based calcium fluorescence assay by use of CHO cells in which the human $S1P_1$ receptor was stably overexpressed (Flp-In system, Invitrogen). In order to enforce G-Protein coupling and to direct signalling towards $Ca^{2+}$ liberation, the overexpressed receptor additionally had a C-terminal sequence of a modified G-protein ($G_{\alpha i4qi4}$) (WO 02/04665). Changes in intracellular calcium were determined by fluorescence measurement with the calcium-sensitive dye fluo-4 (Invitrogen) in a fluorescence imaging plate reader (FlipR, Molecular Dynamics).

CHO cells stably overexpressing the human $S1P_1$ receptor were seeded (40.000 per well) in black clear-bottomed poly-D-lysine-coated 96 well plates (Becton Dickinson, Biocoat cellware) approximately 18-24 h prior to the experiments. Cells were grown in an incubator at 37° C., 5% carbon dioxide and 95% humidity in cell culture media based on F-12 glutamax media (Gibco #31765) supplemented with 1% (vol/vol) penicilline/streptomycine (PAN, #P06-07100), 10% (vol/vol) fetal calf serum (FCS; Hyclone Charcoal/Dextran treated FBS #SH30068) and hygromycin B (Invitrogen, #10687-010) 300 mg/L (final concentrations).

Prior to the FlipR experiment, cells were loaded with fluo-4 acetoxymethyl ester (fluo-4 AM, Invitrogen, #F14202) for 60 min in an incubator at 37° C., 5% carbon dioxide and 95% humidity in dye-loading buffer consisting of Hanks' Balanced Salt Solution (HBSS; Invitrogen #14065049) supplemented with fluo-4 AM at 2 μM (all data given for final concentration), Pluronic® F-127 0.05% (vol/vol) (Invitrogen, #P-3000MP), HEPES 20 mM (Gibco #15630), probenecid 2.5 mM (Sigma #P-8761) and bovine serum albumin (BSA) 0.05% (Sigma # A-6003), adjusted to pH 7.5 with sodium hydroxide. During cell loading, fluo-4 AM is cleaved by intracellular esterase resulting in trapping of the dye fluo-4 within the cells. Loading was terminated by washing of the cells in a cell washer (Tecan Power washer) three times with the buffer specified afore but without fluo-4 AM and BSA. This latter buffer was also used as the buffer in the subsequent cell fluorescence measurements.

The dye-loaded and washed cells were then stimulated with respective compounds with various concentrations added as a solution in DMSO (0.3% vol/vol maximum final concentration of DMSO), or with S1P (100 nM final concentration) in DMSO in the respective concentration only (positive control). Compounds which activated the S1P receptor lead to liberation of intracellular calcium from internal stores resulting in a large transient increase of the fluo-4 fluorescence signal which was monitored over approximately 3 min. The percent activation caused by a test compound was determined from the maximum fluorescence response as compared to the maximum fluorescence response to the S1P positive control. All fluorescence values were corrected for the baseline fluorescence values obtained with cells which were pre-incubated with DMSO only and were not treated with S1P (baseline control). All measurements were performed in triplicate. From the activation at various concentrations, the $EC_{50}$ value was calculated.

2. Chem Cells

The GPCRProfiler® assay from Millipore was used to determine the $EC_{50}$ activity of compound A, BAF-312 and fingolimod on $S1P_1$, $S1P_2$, $S1P_3$, $S1P_4$ or $S1P_5$ receptors. These assays used ChemiScreen GPCR stable cell lines.

3. HSC

Human HSC (Sciencell) were seeded at $25 \times 10^3$ cells per well in 96 multiwell plates, 100 µL/well, and allowed to adhere for 24 hours in complete medium (Sciencell SC5301) with 1% supplements (Sciencell SC5352) and 2% FCS. Culture medium was replaced by Sciencell Medium with 2% FCS but without supplements for another 24 hour period. Cells were washed and placed in 100 µL assay buffer (HBSS, 0.8 mM $MgSO_4$, 20 mM Hepes, 3.3 mM $Na_2CO_3$, 1 mM $CaCl_2$, 10% BSA). Cells were loaded with Fluo4-AM in the presence of pluronic acid for 1 hour at 37° C. in the dark. Loading medium was removed and replaced by 200 µL/well assay buffer. Cells were allowed to stabilize for 20 min at room temperature in the dark. Culture plate was placed in the FlipR instrument, compound A or BAF-312 were added under a volume of 50 µl (5× solution, final concentration 10 µM) and calcium fluorescence was continuously recorded for 6 minutes. For desensitization experiments, after the first injection of compound A or BAF-312, culture plate was washed once and allowed to recover for 1 or 3 hours in assay buffer before the second addition of compound A or BAF-312. For control experiments, first injection of compound A or BAF-312 were replaced by assay buffer and the second injection with compound A or BAF-312 were taken as reference. Results are expressed as Fluorescence Units (FU).

b) β-Arrestin Assay

The PathHunter® β-Arrestin Assay from DiscoverX was used to determine the $EC_{50}$ activity of compound A, BAF-312 and fingolimod on $S1P_1$, $S1P_2$, $S1P_3$, $S1P_4$ or $S1P_5$ receptors. The compounds were tested in assay medium containing 0.5% FBS.

c) GTPγS Assay

This method is described in WO2011/086079.

d) Internalization Assay

The PathHunter® Activated GPCR Internalization Assay from DiscoverX was used to determine the $EC_{50}$ activity of compound A, BAF-312 and fingolimod on the $S1P_1$ receptor. The compounds were tested in assay medium containing 0.5% FBS.

e) cAMP Assay in Chinese Hamster Ovarian (CHO) Cells and HUVEC

1. CHO Cells

The Hit Hunter® cAMP Assay from DiscoverX was used to determine the $EC_{50}$ activity of compound A, BAF-312 and fingolimod on $S1P_1$. The compounds were tested in assay medium containing 0.5% FBS.

2. HUVEC (Human Umbilical Venous Endothelial Cells)

Cyclic AMP in response to compound A, BAF-312 or fingolimod was assessed in Forskolin-treated HUVEC cells by the mean of the cAMP HTRF® kit (Cisbio). Briefly, HUVEC (Lonza) were seeded at $5 \times 10^3$ cells per well into a white 96 multiwell plate (half volume) for 24 hours in EGM2 medium (Lonza). At the beginning of the experiment, EGM2 medium was replaced by assay buffer consisting in HBSS containing Hepes (10 mM), BSA (0.1%) and IBMX (0.5 mM). Cells were allowed to recover during 15 min. Compound A, BAF-312 or fingolimod (10 nM-100 µM) were added to the cells for 15 min followed by addition of forskolin (FSK, 10 µM). After 45 min of FSK treatment, reaction was stopped by addition of MAb anti-cAMP-cryptate and cAMP-D2 for 1 hour. At the end of the incubation, fluorescence was read (Envision, Perkin Elmer) and FRET ratio calculated according to assay kit protocol. The potency of compound A, BAF-312 or fingolimod ($EC_{50}$) was calculated using the Sanofi BIOST@T-SPEED software according to the logistic equation model.

f) Akt and $ERK_{1/2}$ Phosphorylations in RPTEC Cells Assays (Under Basal Conditions or After Tunicamycin Challenge)

RPTEC cells (Lonza) were seeded at $0.3 \times 10^6$ cells per well in 6 multiwell plates in 2 mL per well complete REBM/REGM medium (Lonza) for 24 hours. Cells were starved with serum for an additional 24 hour period in 900 µL quiescent medium. Increasing concentrations of compound A (10×) were added under the volume of 100 µL in each well for 10 minutes at 37° C. When used, tunicamycin (100 µL) was added 30 min prior to compound A addition. After medium removal, cells were rinsed with cold PBS and lysed on ice in 100 µL cold RIPA buffer containing 1% triton, proteases and phosphatases inhibitors. For western blotting, 30 µg of total protein lysate were loaded in 4-12% bis-tris gels (Invitrogen). Following migration and transfer, nitrocellulose membranes were probed with anti phospho-Akt (Phospho-Ser473, Cst #9271) and anti phospho-$Erk_{1/2}$ (phopsho-Tyr202/Tyr204, Cst #4377). Tubuline labelling with anti α-Tubuline (Cst #2144) was used for normalization after densitometric analysis of the films.

g) Akt and $ERK_{1/2}$ Phosphorylations in HUVEC Cells Assays (Under Starvation)

HUVEC cells (Lonza) were seeded at $0.3 \times 10^6$ cells per well in 6 multiwell plates in 2 mL per well complete EGM2 medium (Lonza) for 24 hours. Cells were starved with serum for an additional 24 hour period in 900 µL quiescent medium. Increasing concentrations of compound A, BAF-312 or fingolimod (10×) were added under the volume of 100 µL in each well for 10 minutes at 37° C. After medium removal, cells were rinsed with cold PBS and cells lysed on ice in 100 µL RIPA buffer containing 1% triton, proteases and phosphatases inhibitors. For western blotting, 30 µg of total protein lysate were loaded in 4-12% bis-tris gels (Invitrogen). Following migration and transfer, nitrocellulose membranes were probed with anti phospho-Akt (Phospho-Ser473, Cst #2965) and anti phospho-$Erk_{1/2}$ (Phospho Tyr202/Tyr204, Cst #4377). Tubuline labelling with anti α-Tubuline (Cst #2144) was used for normalization after densitometric analysis of the films.

h) Tunicamycin-Induced Apoptosis Assay

The effect of compound A on tunicamycin (TN)-induced apoptosis in RPTEC was measured by the mean of the Caspase-Glo 3/7 assay kit (Promega). Briefly, RPTEC cells (Lonza) were seeded in 96 multiwell white plates at $30 \times 10^3$ cells per well in REGM (REBM medium plus 0.5% FCS plus Single quots, Lonza) and allowed to adhere for 24 h. After 24 h, complete medium was replaced by serum and supplements free medium (56 µL/well). Cells were pre-treated for 30 min by compound A (final concentrations 0.3-30 µM, 7 µL) followed by addition of tunicamycin (TN, final concentration, 0.1 µg/mL, 7 µL). After 24 hours at 37° C. 5% $CO_2$, 70 µL of Caspase-Glo reagent were added and culture plate placed under shaking for 1 hour. Luminescence was recorded by the mean of the Envision reader (Perkin Elmer). Results are expressed as percent inhibition of TN-induced apoptosis.

i) TNFα-Induced Over-Expression of Adhesion Molecules Assay

ICAM-1, VCAM-1 and P/E-selectins expression were measured in HUVEC by ELISA. HUVEC cells were seeded in 96 multiwell plates at $25 \times 10^3$ cells per well under the volume of 100 μL in EGM2 medium (Lonza) and allowed to adhere for 24 h. After 24 h, complete medium was replaced by quiescent medium (EGM2 without supplements and serum) for 3 hours. Following this, cells were pre-treated with compound A or BAF-312 (1-30 μM) for 18 h. Cells were then treated with TNF-α (3 ng/mL) in growth-factors free medium for an additional 6 h period. Medium was removed and cells were washed and fixed with 100 μL RLC2 solution per well (Alphelys #01-RLC2-RTU30) for 20 min at 4° C. Fixed cells were washed twice with 100 μL HBSS before addition of antibodies anti-ICAM-1 (#BBA3, R&D System), anti-VCAM-1 (#BBA5, R&D System) and anti-P/E-Selectins (#BBA1, R&D system) for 1 hour. Following extensive wash, anti-mouse IgG HRP (#NA931, Amersham) was added for 2 hours. Optical density was read at 450 nm (Envision) after washing and addition of HRP substrate (OPD, Sigma #P9187). Results are expressed as percent inhibition of TNF-α-induced adhesion molecule expression.

j) Impedance Measurement Assay in Chinese Hamster Ovarian (CHO) Cells and Endothelial Cells 1. CHO Cells The Impedance Assay from CEREP was used to determine the $EC_{50}$ activity of compound A, BAF-312 and fingolimod on $S1P_1$.

2. Endothelial Cells

Compound A, BAF-312, fingolimod, SEW2871 and S1P (used as positive control) were concentration-dependent tested on their effect on shape change which is detected by changes in electrical impedance (X-celligence system), to monitor $S1P_1$ receptor desensitization both on human dermal microvascular endothelial cells (HDMEC) and human umbilical vein endothelial cells (HUVEC). On day 1, primary cells were seeded into 96-well e-plates pre-coated with collagen-I with 20,000 cells per well. After 24 h of adherence and proliferation, HDMEC and HUVEC were $1^{st}$ stimulated for 1 h with either S1P (1 μM), compound A (1 μM for HDMEC; 0.1, 1, 10 μM for HUVEC), BAF-312 (1, 10, 100 nM only in HUVEC), fingolimod (100 nM for HDMEC; 1, 10, 100 nM for HUVEC) or SEW2871 (0.1, 1, 10 μM, only in HUVEC). After incubation with the S1PR agonists, the cells were carefully washed twice with medium followed by a 5.5 h recovery period. Then the effect of the preceding $1^{st}$ stimulation on receptor desensitization was assessed using a $2^{nd}$ stimulation of increasing S1P concentrations (0.1, 1 and 10 μM) and measuring the resulting impedance. All measurements were done at least in triplicates. All $1^{st}$ stimulation concentrations were >$EC_{90}$ in HDMEC. Results are expressed in arbitrary impedance unit as mean+/−s.e.m.

5. In Vivo Pharmacology a) Rat Model of Renal Ischemia Reperfusion (I/R) Injury

Male Fischer rats (n=3-9, 250 to 300 g) (Charles River Laboratory, France) received oral administration of compound A at 0.3, 1 and 3 mg/kg or BAF-312 at 3, 10 and 30 mg/kg or vehicle article (methylcellulose 0.6%—tween 80 0.5% in water) within a volume of administration of 2 mL/kg, one hour before renal ischemia. In a second set of experiment, compound A was administrated b.i.d. during 5 days to assess potential tachyphylaxia. Briefly, animals were subjected to sham surgery (i.e. laparotomy, renal arteries isolation) or to 25 min bilateral renal artery occlusion under pentobarbital (50 mg/kg i.p.) anaesthesia. Body temperature (37° C.-38° C.) and hydration (peritoneal injection of physiological serum) were carefully monitored to standardize the surgery procedure and limit inter-individual variability. At the end of the ischemic period, kidneys were reperfused by removing clamps, and the quality of reperfusion was controlled before suturing muscular and cutaneous plan (animals with poor reperfusion were excluded immediately). Twenty-four hours later, blood and kidneys were collected. Blood was centrifuged (3000 g, 10 min) and heparinised plasma frozen for creatinine evaluation using a biochemical analyser (P400, Horiba, France). One kidney was frozen for western blot analyses for tissue albumin (anti-albumin, Santa Cruz) and tissue HSP70 (monoclonal anti-HSP70 antibody from Santa Cruz #SC32239) evaluation and the second one fixed (10% neutral-buffered formalin) and paraffin-embedded for histological analyses on 5 μm-thick slice (acute tubular necrosis quantification using classical hematoxylin-erythrosin-Saffran, modified Masson's trichrome and periodic acid-Schiff associated blue alcine) and immunohistochemistry analyses (macrophage staining with monoclonal anti-CD68 antibody from Acris #BM4000, and capillary staining with monoclonal ant-PECAM antibody from Santa Cruz #SC1506, using Ventana robot, VMS Inc.). Acute tubular necrosis is expressed as percentage of tubules that displayed cell necrosis in 12-15 fields in renal corticomedullary region. CD68 and PECAM immunolabeling are expressed as percentage of positive pixel count (Aperio algorithm) on whole section. Plasma creatinine is expressed as mean+/−s.e.m.

b) Mouse Model of Rhabdomyolysis-Induced Renal Injury

Swiss (CD1) male mice (n=5-15, 13-14 weeks old) (Charles River Laboratory, France) received oral administration of compound A at 0.3, 1, 3 and 10 mg/kg or vehicle article (methylcellulose 0.6%—tween 80 0.5% in water) within a volume of administration of 10 mL/kg, one hour before glycerol injection. Intramuscular injection of glycerol (50% in PBS v/v) or vehicle article (PBS) was performed into hindlimbs (2 injections per leg, gastrocnemius and rectus femoris) at 8 mL/kg under pentobarbital (33 mg/kg) and ketamine (40 mg/kg) anaesthesia. Twenty-four hours later, blood was collected, centrifuged (3000 g, 10 min) and heparinised plasma frozen for creatinine evaluation using a biochemical analyser (P400, Horiba, France). Results are expressed as mean+/−s.e.m.

Results

The compound according to the invention, namely compound A, was the subject of various in vitro and in vivo experiments in order to demonstrate its activity in AKI settings, and its differentiation over $S1P_1$ functional antagonists.

1—Cardiovascular Function Safety

Although compound A is a $S1P_1$ agonist that lacks functional antagonism, potential target-based concerns could be similar to the $S1P_1$ functional antagonists. The greatest clinical experience to date has been generated with the mixed $S1P_{1/3/4/5}$ compound, fingolimod, which induces atrio-ventricular block and bradycardia (Schmouder et al., 2006, J Clin Pharmacol 46: 895-904). There is much preclinical evidence implicating $S1P_3$ in these cardio-toxicity findings, hence the field has moved to identification of selective $S1P_1$ compounds to overcome these limitations. However, selective $S1P_1$ compounds, that follow into the clinical phase appear to also induce bradycardia (Gergely et al., 2012, BJP 167: 1035-1047), but their effects on atrio-ventricular block are currently unknown. Thus a number of studies were conducted in addition to the usual studies to evaluate potential cardiotoxicity of compound A. In the hERG assay, the $IC_{50}$ for compound A was >30 μM. In the rabbit Purkinje fiber assay, there was no significant effect of compound A tested from 0.3 to 10 μM, although a shortening of the action potential was observed at 26 μM.

No effect on heart rate or atrioventricular block or any other ECG parameters was observed in a dog telemetry study, at 30 or 100 mg/kg p.o. and 10 or 30 mg/kg i.v. (infusion over 30 min). There was no significant change in blood pressure at both doses.

2—In Vivo Renal Pharmacology

A rat model of renal ischemia reperfusion (I/R) injury was used to mimic the renal injury arising after cardiac surgery in patients. In this model, compound A reduced markedly (85-90%) the severity of AKI, as reflected by limiting the rise of serum creatinine (a clinically-validated biomarker) (FIG. 1A is representative of 5 independent studies). The effect was dose-dependent and statistically significant at 1 and 3 mg/kg p.o. (FIG. 1A). Histological analysis showed that compound A had direct effects on the vasculature by preventing albumin extravasation (FIG. 1C) and preserving capillaries. Compound A also protected renal proximal tubules from necrosis, reduced macrophages infiltration and increased renal HSP70 protein (a marker associated with repair following renal ischemic injury). Compound A showed no sign of tachyphylaxis as similar activity was retained following 5 days of repeated BID administration compared to a single administration (FIG. 1D).

Rhabdomyolysis is another significant cause of AKI in patients and is reproduced in mice by the intramuscular injection of glycerol. Glycerol induces a progressive muscle injury with release of myoglobin and subsequent renal dysfunction. As observed in the I/R model, compound A prevented markedly (~85% at 10 mg/kg p.o) and dose-dependently the deterioration of renal function in this model (n=3 independent studies) (FIG. 2).

The effects of compound A were compared in the renal ischemia reperfusion model with a $S1P_1$-selective functional antagonist, BAF-312. BAF-312 is at least 10-fold more potent in most $S1P_1$ in in vitro assays (including endothelial assays—see table 1) and has similar plasma/kidney exposure to compound A in rats. However, despite the improved potency/exposure properties of BAF-312, it failed to show more than a 40% reduction in serum creatinine in the ischemia reperfusion model, even at doses up to 30 mg/kg p.o. (FIG. 1B).

3—Differentiation on Lymphopenic Activity

S1P is responsible for the egress of lymphocytes from the lymph node to the blood through $S1P_1$ activation. This $S1P_1$ activation causes receptor internalization followed by recycling of the receptor back to the cell surface, allowing re-activation. However, $S1P_1$ functional antagonists (fingolimod, BAF-312) cause degradation of the internalised $S1P_1$ and hence cause dramatic and sustained reductions in cell surface $S1P_1$. Consequently, $S1P_1$ functional antagonists show a large and sustained drop in blood lymphocytes as observed preclinically and clinically (Mandala et al., 2002, Science 296: 346-349; Gergely et al., 2012, BJP 167: 1035-1047).

As expected, BAF-312 induced a profound (−80%) and sustained lymphopenia in rats (FIGS. 3A, 3B). This was evident even at doses as low as 1 mg/kg p.o. (the lowest dose tested). The 2 doses that were partially effective in the rat AKI model were higher doses (10 and 30 mg/kg p.o., FIG. 1B) and represent highly lymphopenic doses. In contrast, compound A at 1 and 3 mg/kg p.o. showed no lymphocyte reduction, even following 5 days of repeated BID administration (3 mg/kg p.o) in rat (FIG. 3C). Higher doses of compound A revealed a dose-dependent lymphopenia, but these represent higher than required doses for full AKI protection.

Similarly, no lymphopenic activity of compound A was observed in mice at 3 and 10 mg/kg (FIG. 4), doses which were active in the glycerol-induced rhabdomyolysis model (FIG. 2).

Compound A was non-lymphopenic in dogs at 3 mg/kg p.o. (FIG. 5A). This non-lymphopenic dose in dogs already provides an exposure (Cmax and AUC) that exceeds the exposure required for full AKI protection in rats (3 mg/kg) (table 4). At the higher doses of 10 and 30 mg/kg p.o in dogs compound A induced only a transient lymphopenia (FIG. 5A). In contrast, BAF-312 induced a profound ($I_{max}$ ~80%) reduction in lymphocytes at 3 mg/kg p.o. which took at least 60 days to recover (FIG. 5B).

Compound A is a unique $S1P_1$ agonist because it demonstrates for the first time a strong AKI protection at non-lymphopenic doses (FIG. 3D). Although other $S1P_1$ compounds, such as fingolimod and SEW2871, are also active in AKI models, their effects occur at lymphopenic doses (Awad et al., 2006, Am J Physiol Renal Physiol 290: F1516-F1524; Sanna et al., 2004, JBC 279: 13839-13848; Lai et al., 2007, Kidney Int 71: 1223-1231).

These in vivo data support that compound A acts as a $S1P_1$ agonist inducing AKI protection at non-lymphopenic doses. Compound A differs notably from BAF-312, as described herein, as well as other $S1P_1$ functional antagonists which are specifically designed to be lymphopenic agents for example for autoimmune diseases.

4—Differentiation on Endothelial Barrier Integrity $S1P_1$ functional antagonism is associated with endothelial-damaging effects. Macular and lung oedema are prominent adverse events in multiple sclerosis patients treated with fingolimod (Jain and Bhatti, 2012, 78: 672-680).

We found that chronic oral administration in healthy mice of fingolimod was able to produce significant vascular leakage (FIGS. 6A, 6B), in line with the clinical findings. The selective $S1P_1$ agonist, BAF-312 at 1 and 3 mg/kg b.i.d. induced an even greater vascular leakage in the lung (FIGS. 6A, 6B). These findings are in agreement with previous reports demonstrating that $S1P_1$ functional antagonists altered endothelial barrier integrity and promoted vascular protein extravasation in the lung (Shea et al., 2010, Am J Respir Cell Mol Biol 43: 662-673). In contrast compound A showed no increase in vascular leakage (at 3 and 10 mg/kg (representing doses providing up to the full AKI protective effect in mice) (FIGS. 6A, 6B). Similarly in Fisher rats, compound A did not induce lung vascular leakage at 1 and 3 mg/kg (representing AKI effective doses) or even one dose higher (10 mg/kg). In contrast, BAF-312 induced vascular leakage in rats at both 3 mg/kg (non-effective AKI dose) as well as 30 mg/kg (partially effective AKI dose).

Given the observed endothelial-damaging properties of BAF-312 (FIG. 6), the protective properties of BAF-312 could be counteracted by its endothelial deleterious effects resulting in the partial protective effect observed (FIG. 1B). Endothelial damage is a notable feature of multiple $S1P_1$ functional antagonists (FIG. 6 and published data). The novel profile of compound A therefore provides the opportunity to protect against acute kidney injury at doses that are endothelial protective rather than damaging.

5—In Vitro Pharmacology

Compound A was shown to be a potent $S1P_1$ agonist. In CHO cells over-expressing human $S1P_1$ (G-fusion), $EC_{50}$ was 31 nM in a calcium mobilization assay, 656 nM in a β-arrestin assay, 206 nM in GTPγS assay and 213 nM in an internalization assay (table 1).

TABLE 1

EC$_{50}$ values for compound A, BAF-312 and fingolimod using various in vitro assays.

| Assay | Cell type | Proteins in assay media | EC$_{50}$ in nM | | | | |
| --- | --- | --- | --- | --- | --- | --- | --- |
| | | | Compound A | BAF-312 | Fingolimod phosphate | S1P | SEW2871 |
| FLIPR | Chem# | 0% | 86 | 29 | 26 | 9.6 | — |
| | CHO | 0% | 31 | 2.8 | 0.14 | 7.5 | 24 |
| GTPγS | CHO | 0% | 206 | 6.7 | 5 | 120 | 795 |
| β-arrestin | CHO | 0.5% FBS | 656* | 5.4* | 7 | 30.9* | — |
| Internalization | CHO | 0.5% FBS | 213* | <0.59* | 2.72* | 48.1* | — |
| cAMP | CHO | 0.5% FBS | 22.6 | 0.47 | — | 78 | — |
| cAMP | HUVEC | 0.1% BSA | 15,600 | 74 | 132 | — | — |
| pERK1/2 | HUVEC | 0.1% FBS | 190 | 4.9 | 9.4 | — | — |
| pAkt | HUVEC | 0.1% FBS | 101 | 4.3 | 14.5 | — | — |
| Impedance | CHO | 10% FBS + 0.1% BSA | 65 | 0.4 | — | 1.5 | — |
| Impedance | HUVEC | 2% FBS | 172 | 0.21 | 0.12 | — | 54 |

Chem* and CHO cells were engineered to over-express human S1P$_1$.
HUVECs endogenously express S1P$_1$.
ChemiScreen assay.
"—" means not determined.
*Values are means of 2 separate experiments.
β-arrestin assay: Cpd A-800 & 511, BAF-312-7.9 & 2.83, S1P-41 & 20.8;
internalisation assay: Cpd A-160 & 266, BAF-312-<0.5 & 0.67, fingolimod-P-0.7 & 4.74, S1P-56 & 40.2.

Compound A displayed no functional antagonism properties nor induced receptor desensitization (FIGS. 7-10). This differentiation was demonstrated in four independent in vitro systems, two systems using impedance measurement in endothelial cells HDMEC (human dermal microvascular endothelial cells) and HUVEC (human umbilical vein endothelial cells), and two systems using FlipR assay in CHO cells and HSC cells (hepatic stellate cells). Pre-incubation with compound A (followed by a wash step) allowed an almost complete 2$^{nd}$ stimulation with S1P (FIGS. 7-9) or compound A (FIG. 10). However, pre-incubation with the functional antagonists prevented a full 2$^{nd}$ stimulation with S1P (FIGS. 7-9) or BAF-312 (FIG. 10). In the HUVEC impedance assay, the concentration in that each compound began desensitizing the S1P$_1$-induced impedance response was compared to its absolute EC$_{50}$ in the assay. BAF-312 began desensitization at 5× the EC$_{50}$, SEW2871 at 20× the EC$_{50}$, while no desensitization was observed for compound A up to 60× the EC$_{50}$.

The data in FIGS. 7-10 indicate that the functional antagonists (fingolimod, BAF-312, SEW2871 and ponesimod) induced sustained receptor desensitization.

Compound A displayed different relative potencies on S1P$_1$ signalling pathways (table 1) compared to BAF-312 or fingolimod. Since the assay conditions with respect to protein differed between the tests, we excluded the possible influence of protein binding on the relative potencies by comparing the potencies in CHO assays for cAMP, beta arrestin and internalisation using the same media conditions. As shown in table 2, compound A (in relation to BAF-312 and S1P) is more biased on its activation of cAMP compared to internalisation or β-arrestin.

TABLE 2

Relative EC$_{50}$ values of compound A, BAF-312 and S1P (normalized to cAMP assay). Media contained identical protein concentrations (0.5% FBS) in the 3 tests

| | cAMP CHO | Internalization CHO | β-Arrestin CHO |
| --- | --- | --- | --- |
| Compound A | 1 | 9.4 | 29 |
| BAF-312 | 1 | 1.3 | 11.5 |
| S1P | 1 | 0.62 | 0.40 |

Compound A induced survival markers, pERK and pAKt, in human renal tubular epithelial cells (RPTEC) with an EC$_{50}$ around 3 μM under basal conditions, or after tunicamycin injury (EC$_{50}$~10 μM) in a concentration-dependent manner. These pro-survival effects were more potent in human endothelial cells after serum starvation, with an EC$_{50}$ of 101 nM on P-Akt, and 190 nM on P-ERK$_{1/2}$. Moreover compound A inhibited tunicamycin-induced apoptosis in RPTEC evaluated by the caspase 3/7 activity with an EC$_{50}$ around 3-10 μM.

Compound A, unlike BAF-312, reduced TNFα-induced over-expression of adhesion molecules, including ICAM-I, VCAM-I, and P/E selectins, on three human endothelial cell types (HPAEC, HUVEC and HRGEC). These endothelial dysfunction markers are known to be upregulated in plasma samples from AKI patients (Sadik et al., 2012, Mol Cell Biochem 359:73-81), and involved in the infiltration process of inflammatory cells into the tubulo-interstitium space.

Compound A had an attractive selectivity profile on the other receptors in the S1PR family (table 3), on over 110 targets in a CEREP panel, on over 216 kinases and on over 5 targets in an ion channel panel. As shown in table 3, Compound A is a more selective S1P$_1$ agonist compared to fingolimod. The lack of activity on S1P$_2$ and S1P$_3$ is particularly important as these receptors are reported to oppose the function of S1P$_1$ on endothelial cells.

TABLE 3

Selectivity of compound A, BAF-312 and fingolimod against members of the sphingosine receptor family.

| | $EC_{50}$ in μM | | | | | | | |
|---|---|---|---|---|---|---|---|---|
| | $S1P_2$ | | $S1P_3$ | | $S1P_4$ | | $S1P_5$ | |
| | FlipR (Chem) | β-arrestin | FlipR (Chem) | β-arrestin | FlipR (Chem) | β-arrestin | FlipR (Chem) | β-arrestin |
| Compound A | >30 | >10 | >30 | >10 | >30 | 2.5 | 1.0 | 1.3 |
| BAF-312 | >30 | >10 | >30 | >10 | >30 | 2.1 | 0.30 | 0.035 |
| Fingolimod | >30 | — | 0.82 | — | 0.12 | — | 0.12 | — |

"—" means not determined.

The preferential activation of some signalling pathways by compound A (e.g. cAMP), while having weaker potency on others (e.g. internalisation, β-arrestin), provides the desired profile for AKI (i.e. minimal receptor desensitization, no sustained lymphopenia, endothelial protection). This is in contrast to that desired for the $S1P_1$ functional antagonists BAF-312 and fingolimod in multiple sclerosis (high receptor desensitization, strong lymphopenia—with endothelial damage being the undesired side effect). This profile defines compound A as a novel class of biased $S1P_1$ agonist.

TABLE 4

Pharmacokinetic properties of compound A at 3 mg/kg p.o. in male Fisher rat and beagle dog.

| | Rat | Dog |
|---|---|---|
| Cmax (μg/mL) | 2.56 | 2.91 |
| AUC (μg · h/mL) | 13 | 41.3 |

CONCLUSION

These preclinical data demonstrate a profound impact of compound A on multiple mechanistic endpoints in AKI, including a marked maintenance of the endothelial barrier function, as well as a reduction of tubular necrosis and macrophage inflammation. All AKI-protective doses of compound A (in both mice and rats) were non-lymphopenic and when the corresponding exposures were achieved in dogs, compound A was still non-lymphopenic. Since compound A was non-lymphopenic at all AKI-protective doses, its mechanism of AKI protection is independent of lymphopenia. Compound A showed direct protective effects on endothelial and epithelial cells, which are likely the mechanism of action in AKI.

This is in contrast to existing $S1P_1$ compounds which have a different signalling profile and are i) $S1P_1$ functional antagonists, ii) endothelial-damaging and iii) show only limited activity in I/R-induced AKI at doses that are lymphopenic.

Compound A provides the novel opportunity to treat AKI patients without inducing lymphopenia and hence avoiding the corresponding side effects (including infections). Consequently, this compound has the potential to be a transformative therapy in a field where there are currently no drugs available to patients.

The invention claimed is:

1. A method of treating AKI (acute kidney injury) in a patient in need thereof comprising administering to said patient a therapeutically effective amount of {4-[5-(3-chloro-phenoxy)-oxazolo[5,4-d]pyrimidin-2-yl]-2,6-dimethyl-phenoxy}-acetic acid, or a pharmaceutically acceptable salt thereof, wherein the administration of the therapeutically effective amount of {4-[5-(3-chloro-phenoxy)-oxazolo[5,4-d]pyrimidin-2-yl]-2,6-dimethyl-phenoxy}-acetic acid, or a pharmaceutically acceptable salt thereof, does not induce lymphopenia.

2. The method of claim 1, wherein the lymphopenia is limited lymphopenia.

3. The method of claim 1, wherein treating AKI reduces plasma creatinine by at least 30%.

* * * * *

UNITED STATES PATENT AND TRADEMARK OFFICE
CERTIFICATE OF CORRECTION

PATENT NO. : 9,782,411 B2  
APPLICATION NO. : 15/027964  
DATED : October 10, 2017  
INVENTOR(S) : Véronique Briand et al.

Page 1 of 1

It is certified that error appears in the above-identified patent and that said Letters Patent is hereby corrected as shown below:

On the Title Page

Page 2, Section "OTHER PUBLICATIONS", left-hand side column, Line 17:  
Please replace "Ill" with --Ill--;

Page 2, Section "OTHER PUBLICATIONS", left-hand side column, Line 41:  
Please replace "SiP$_2$" with --S1P$_2$--;

Page 2, Section "OTHER PUBLICATIONS", right-hand side column, Line 10:  
Please replace "Sphinogosine" with --Sphingosine--;

Page 2, Section "OTHER PUBLICATIONS", right-hand side column, Lines 39-40:  
Please replace "S1P1 and SIP3" with --S1P$_1$ and S1P$_3$--; and Page 2, Section "OTHER PUBLICATIONS", right-hand side column, Line 62:  
Please replace "Phospate" with --Phosphate--.

Signed and Sealed this  
Twenty-second Day of May, 2018

Andrei Iancu  
*Director of the United States Patent and Trademark Office*